US009589219B1

(12) United States Patent
Gonzales, Jr.

(10) Patent No.: US 9,589,219 B1
(45) Date of Patent: Mar. 7, 2017

(54) METHOD AND SYSTEM FOR MAGNETIC STRIPE READING USING MOBILE MAGNETOMETERS

(71) Applicant: eBay Inc., San Jose, CA (US)

(72) Inventor: Sergio Pinzon Gonzales, Jr., San Jose, CA (US)

(73) Assignee: eBay Inc., San Jose, CA (US)

( * ) Notice: Subject to any disclaimer, the term of this patent is extended or adjusted under 35 U.S.C. 154(b) by 0 days.

(21) Appl. No.: 14/963,639

(22) Filed: Dec. 9, 2015

(51) Int. Cl.
G06K 19/06 (2006.01)
G06F 19/00 (2011.01)

(52) U.S. Cl.
CPC ..... *G06K 19/06187* (2013.01); *G06F 19/322* (2013.01)

(58) Field of Classification Search
None
See application file for complete search history.

(56) References Cited

U.S. PATENT DOCUMENTS

2015/0069126 A1* 3/2015 Leon ............... G06K 19/06206 235/449

* cited by examiner

*Primary Examiner* — Kristy A Haupt
(74) *Attorney, Agent, or Firm* — Schwegman Lundberg & Woessner, P.A.

(57) ABSTRACT

In various example embodiments, a system and method for reading magnetic information by a mobile device are presented. In example embodiments, the mobile device comprises a housing having an integrated surface for swiping a magnetic swipe card and a magnetometer, positioned within the housing, for detecting direction and strength of magnetic fields to read magnetic information from a variety of sources and to produce digital magnetometer output signals. The digital magnetometer output signals represent magnetic information derived from the magnetic swipe card and from the Earth's magnetic fields (or other sources). Each of the digital magnetometer output signals having a magnitude related to the strength of the detected magnetic fields. The mobile device determines at least some of the digital magnetometer output signals represent the magnetic information derived from the magnetic swipe card and provides that information to a magnetic card application for processing. The mobile device determine at least some of the digital magnetometer output signals represent the magnetic information derived from the Earth's magnetic fields and provides that information to a compass application for processing.

18 Claims, 10 Drawing Sheets

METHOD AND SYSTEM FOR MAGNETIC STRIPE READING USING MOBILE MAGNETOMETERS

TECHNICAL FIELD

Embodiments of the present disclosure relate generally to data processing and, more particularly, but not by way of limitation, to a method and system for magnetic stripe reading using mobile magnetometers.

BACKGROUND

Conventionally, mobile devices such as smart phones may include magnetometer used as a compass. For example, starting with the iPhone 3GS, all iPhones have a built-in magnetometer. The magnetometer in the iPhone is used to find the direction the iPhone is pointed in (e.g., a compass). By knowing the direction the iPhone is pointed in (by measuring the direction of the Earth's magnetic field), along with global positioning systems (GPS), allows users to use navigation apps on their iPhones.

BRIEF DESCRIPTION OF THE DRAWINGS

Various ones of the appended drawings merely illustrate example embodiments of the present disclosure and cannot be considered as limiting its scope.

The headings provided herein are merely for convenience and do not necessarily affect the scope or meaning of the terms used.

DETAILED DESCRIPTION

The description that follows includes systems, methods, techniques, instruction sequences, and computing machine program products that embody illustrative embodiments of the disclosure. In the following description, for the purposes of explanation, numerous specific details are set forth in order to provide an understanding of various embodiments of the inventive subject matter. It will be evident, however, to those skilled in the art, that embodiments of the inventive subject matter may be practiced without these specific details. In general, well-known instruction instances, protocols, structures, and techniques are not necessarily shown in detail.

Figure 2:
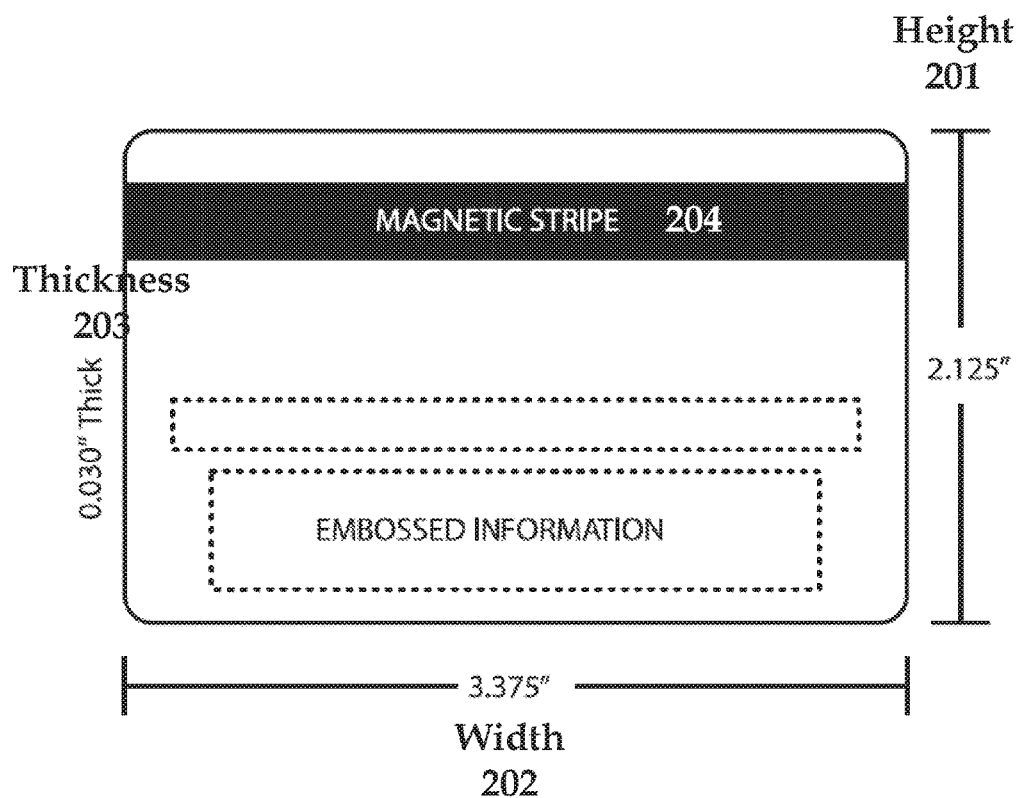
FIG. 2 illustrates an example of a magnetic stripe on a magnetic swipe card used in financial transactions, according to an example embodiment.

In various example embodiments a mobile device includes a housing having an integrated surface configured to align magnetic information stored in a magnetic stripe on a magnetic swipe card by moving the magnetic swipe card across the integrated surface of the mobile device for reading the magnetic information. FIG. 2 illustrates an example of a magnetic stripe from a magnetic swipe card for a financial transaction card (e.g., credit and banking cards). The magnetic swipe cards can also be used as identify cards (e.g., driver's licenses), security badges, transportation tickets, loyalty cards, etc. The magnetic stripes represent tracks of iron-based magnetic particles that are encoded to orient to one of the magnetic pole positions (e.g., North or South). The flux reversals that results as the magnetic signal is read across the magnetic stripe results in a code that can be interpreted by a reader (e.g., a magnetometer). Accordingly, the magnetic stripes on the magnetic swipe cards use a strip of magnetic material to store digital data. A small amount of data is stored on the strip, may include the cardholder's name, account number, expiration date, etc.

In example embodiments, the mobile device is a smart phone and the integrated surface is the backside of the smart phone. The integrated surface is positioned, at least partially, above a magnetometer inside the mobile device. The magnetometer represents a magnetic reader. In some embodiments, the built-in magnetometer in a mobile device is used to pick up the flux reversals in a magnetic stripe as the magnetic swipe card is swiped across the backside of the mobile device.

In further embodiments, the built-in magnetometer may be calibrated to pick up the flux reversals in a magnetic stripe as the magnetic swipe card is swiped across the backside of the mobile device. In other embodiments, the digital magnetometer output signals may be calibrated by a processor executing an algorithm. Calibrations may be used to account for various environmental factors such as the Earth's magnetic field, electric currents in the ionosphere, temperature, and hard and soft iron distortions. For example, to calibrate for the Earth's magnetic field, the device's location (e.g. via GPS) can be found and used to compare the device's location to the known magnetic strength at that location on the Earth, measured in Gauss units (this can be converted to Tesla). Slight variations in the ionosphere can influence the Earth's magnetic field on the order of 0.2-0.3 mGauss (average). Temperature can also factor into magnetic readings and must also be factored into the algorithm. Hard and soft iron distortions result from objects in the magnetic field; distinctions between hard and soft iron distortions pertain to the specific material of the object. In the context of a mobile device, the internal components that surround the magnetometer must also be factored into the algorithm and will vary from device to device as their components vary. Secondary distortions can occur from other objects, like the human body.

In further embodiments, a magnetometer is used to read information by detecting a direction and strength of magnetic fields from the Earth and magnetic fields from the magnetic card information for generating digital magnetometer output signals. In some embodiments, the magnetometer is an integrated circuit compass chip located within the mobile device that may be able detect magnetic fields from a variety of magnetic sources, for example magnetic card information from magnetic swipe cards as well as the Earth's magnetic fields.

In various embodiments, the magnetometer produces the digital magnetometer output signals associated with the magnetic card information and other magnetic sources. In some embodiments, the other digital magnetometer output signals represent the digital magnetometer output signals associated with the Earth or associated with medical information related to a human body of a person or user. In other embodiments, a processor within the mobile device performs a filtering function for filtering the digital magnetometer output signals derived from various magnetic sources. In various embodiments, the filtering may be performed based on the magnitude of the digital magnetometer output signals. In various embodiments, the magnitude of the digital magnetometer output signals are associated with the strength of the magnetic fields detected or measured by the magnetometer. In various embodiments described, the direction of the magnetic fields may be represented by x, y, and z directional vectors.

In other embodiments, the magnetometer includes an analog-to-digital converter for providing digital magnetometer output signals associated with the magnetic card information and digital magnetometer output signals associated with the earth, and magnetic sources.

In other example embodiment, the mobile device includes a processor that receives the digital magnetometer output signals, and may perform further processing (e.g., calibrations, filtering, etc.) before utilizing the digital magnetometer output signals in various applications, such as apps executing on a mobile device. The digital magnetometer output signals may be associated with the different magnetic sources, for example, the magnetic card information, the Earth, or medical information associated with the human body. In various embodiments, the processor from the mobile device determines which digital magnetometer output signals are to be provided to which application installed and/or executing on the mobile device, or some other computing device. For example, the mobile device may receive some sort of indication to provide the digital magnetometer output signals to a particular application. One indication may be when a particular application (e.g., a magnetic swipe card application) is open on the mobile device, such that the relevant digital magnetometer output signals (e.g., those signals associated with the magnetic card information) are sent to that application by the processor in the mobile device.

In some embodiments, the digital magnetometer output signals are associated with the magnetic card information, and the processor in the mobile device is used to decode the magnetic information associated with the magnetic card information and to make digital signals available to a magnetic swipe card application when the processor of the mobile device is executing instructions from the magnetic swipe card application. In other embodiments, the digital magnetometer output signals are associated with other magnetic information from other magnetic sources, and the processor in the mobile device is further configured to make those signals available to other applications when the processor of the mobile device is executing instructions from the other applications. Examples of other applications include a compass application that uses the digital magnetometer output signals associated with the Earth, a medical application (e.g., a blood application or a body fat application) that uses the digital magnetometer output signals associated with the medical information from a human body.

In other example embodiments, some or all of the components of the magnetic swipe card application may be running on another computing device and may access the digital magnetometer output signals associated with the magnetic card information.

In a further embodiment, a method of magnetic stripe reading using a mobile device is described. The method includes reading magnetic card information by swiping a magnetic stripe on a magnetic swipe card along a surface of a mobile device positioned partially over a magnetometer. The magnetometer within the mobile device reads the magnetic card information and also detects other magnetic information from other magnetic sources (e.g., the Earth, human bodies, electronics, or other items in the environment). The magnetometer within the mobile device generates digital magnetometer output signals. A processor of a machine determines at least some of the digital magnetometer output signals represent encoded magnetic card information and at least some of the digital magnetometer output signals represent the other magnetic information detected. A processor of a machine executes at least one of a magnetic card information application and another magnetic application. The magnetic card information application utilizes the encoded magnetic card information and the other magnetic application utilizes the other magnetic information detected in example embodiments.

In another embodiment, a method of magnetic stripe reading using a mobile device is described. A magnetometer included within a mobile device detects magnetic information. At least some of the magnetic information is decoded by a processor of a machine. A processor of a machine filters the magnetic information to determine magnetic card information associated a magnetic card application and Earth's magnetic field information associated with a compass application. In response to instructions executing on the processor of the machine from the magnetic card application, the magnetic card information is accessed. In response to instructions executing on the processor of the machine from the compass application, the Earth's magnetic field information is accessed.

Figure 1:
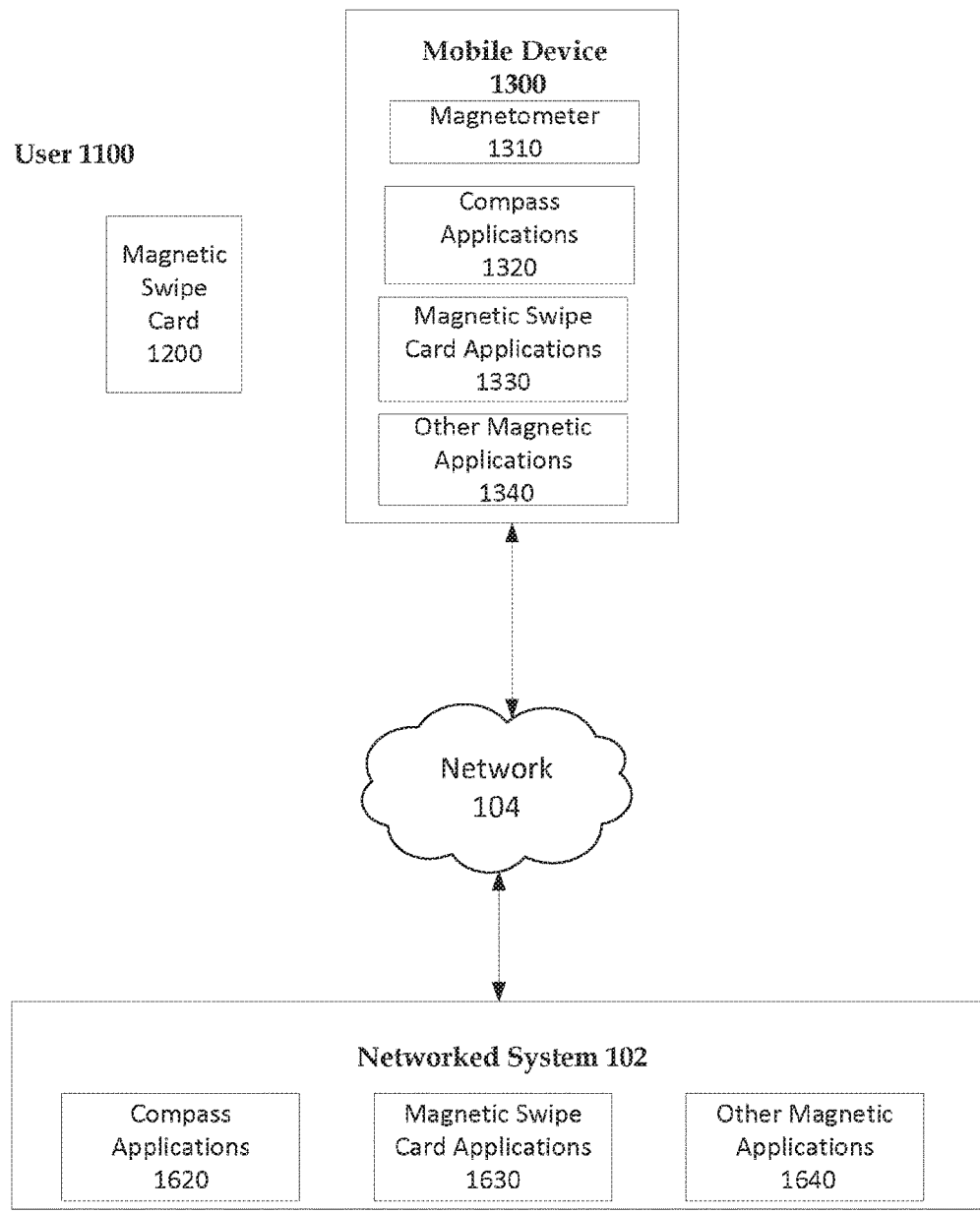
FIG. 1 is a high level block diagram illustrating a system for reading magnetic information from a magnetic swipe card and utilizing the magnetic information in various applications, according to some example embodiments.
Figure 7:
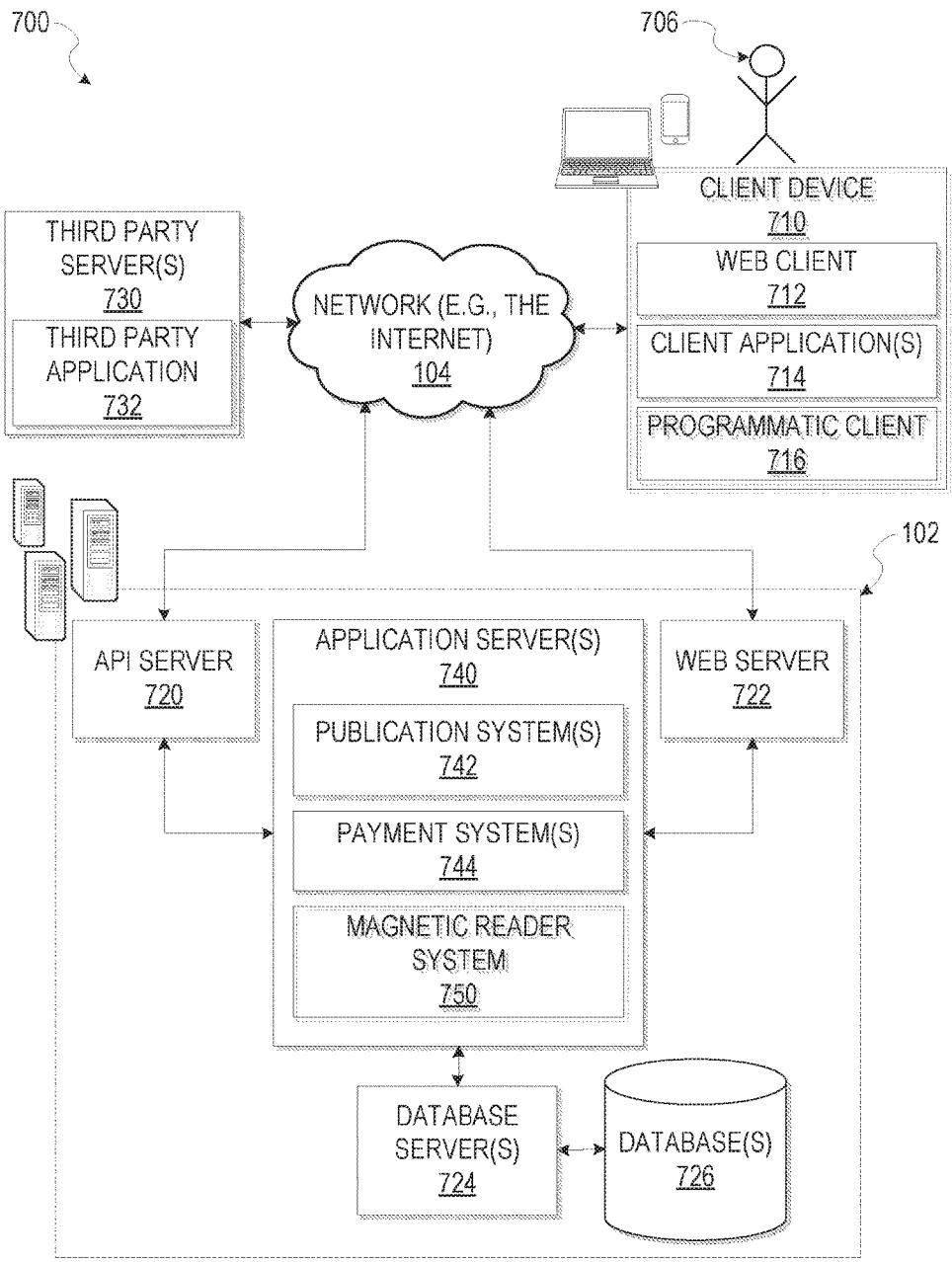
FIG. 7 is a block diagram illustrating a networked system, according to some example embodiments.

FIG. 1 illustrates a system for reading magnetic information from a magnetic swipe card according to an example embodiment. The system 1000 includes a mobile device 1300 communicatively coupled to a networked system 102 via a network 104. The networked system 102 includes one or more remote servers and associated databases. In example embodiments, the mobile device 1300 may represent a client device 710, as shown in FIG. 7. The networked system 102, the network 104 and the mobile device 1300 (represented by the client device 710) are described in further detail in conjunction with the embodiment described in FIG. 7.

A magnetic swipe card 1200 represents a type of card capable of storing data by modifying the magnetism of tiny iron-based magnetic particles on a band of magnetic material on the card (also referred to as the magnetic stripe or magstripe). The data from the magnetic stripe is read by swiping the magnetic stripe past a magnetic read head. A magnetometer 1310 represents an example of a read head, also referred to as a reader.

In the embodiment shown in FIG. 1, a user 1100 has a magnetic swipe card 1200 that he or she swipes across a mobile device 1300. For example, the mobile device 1300 represents a smart phone that has a back side or surface that can be used to swipe the magnetic swipe card 1200 by moving the magnetic swipe card 1200 across the back surface. In various embodiments, the surface used for swiping is integrated with the mobile device 1300, and not an external device (e.g., a dongle) connected via an earphone jack of a mobile device 1300 or other type of reader. At least a portion of the back surface of the user device 1300 is positioned over a magnetometer 1310 for reading the magnetic card information from the magnet swipe card 1200.

The mobile device 1300 includes a built-in magnetometer 1310 and has a variety of applications installed on the mobile device 1300 (e.g., as shown in FIG. 1) that can use magnetic information encoded in the magnetic swipe card 1200 and other magnetic information sensed by the magnetometer 1310. The other information sensed or detected by the magnetometer 1310 may include, for example, magnetic information related to the Earth's magnetic fields, magnetic information related to a user or human body, or magnetic information related to electronic components.

Various magnetometers have different sensitivities and can measure a range of magnetic fields originating from a various magnetic sources. Thus, depending on the sensitivity of the magnetometer within the mobile device determines which magnetic fields are detected. Examples of other magnetic sources and associated strengths (or magnitudes) of their magnetic fields include pulsed fields (e.g., 40-60 teslas); electromagnets (e.g., 2-5 teslas); Earth's fields (e.g., between $10^{-5}$ to $10^{-4}$ teslas); traffic, appliances, etc. (e.g., between $10^{-6}$ to $10^{-5}$ teslas); power transmission lines at 10 meters (e.g., between $10^{-8}$ to $10^{-7}$ teslas); human hear signals (e.g., between $10^{-10}$ to $10^{-9}$ teslas); optic nerve signals (e.g., between e.g., $10^{-12}$ to $10^{-11}$ teslas); and muscle impulses and spontaneous brain activity (e.g., in the range of $10^{-12}$).

These magnetic fields may be generated by a variety of magnetic sources such as a human body (e.g., a heart and brain of a person, muscle impulses, and optic nerve signals), a magnet, various electrical/electronic appliances including TVs and computers, power transmission lines, etc. The Earth also has its own magnetic field with its largest at the poles (~60 000 nanoteslas (nT)) and it is smallest as the equator (~30 000 nT). These examples of magnetic signals generated by a variety of sources, other than the magnetic swipe card 1200, are referred to as other magnetic information throughout the specification. Various embodiments described throughout the specification, filter the magnetic information such that the magnetic information derived from the different sources can be determined or identified. The digital magnetometer output signals that are filtered are then sent to relevant applications or apps. In other embodiments, calibration is used to correct for deviations (caused by magnetic fields from other sources) in the detected magnetometer signals.

The information detected, sensed or measured by the magnetometer 1310 may be used by a number of applications installed on the mobile device 1300. As shown in FIG. 1, in an example embodiment, the mobile device 1300 may have at least one of the following applications or types of applications installed on it: compass applications 1320, magnetic swipe card applications 1330, and other magnetic applications 1340 (e.g., medical applications). The compass applications may use information from the digital magnetometer output signals associated with the Earth's magnetic field. The magnetic swipe card applications (e.g., payment applications, banking applications, security applications, travel applications, and ticketing applications) may use information from the digital magnetometer output signals associated with magnetic stripes on a magnetic swipe card. The medical applications may use information in the digital magnetometer output signals associated with the human body (e.g., heart, brain, blood, muscles, and nerves).

In some examples, the digital magnetometer output signals associated with the Earth's magnetic field have magnitudes within a first range; the digital magnetometer output signals associated with magnetic stripes on a magnetic swipe card have magnitudes within a second range; and the digital magnetometer output signals associated with the human body have magnitudes within a third range. There may be some overlap with one or more of the first, second and third ranges. In various embodiment, filtering may be based on the magnitude ranges of the digital magnetometer output signals. For example, digital magnetometer output signals having a magnitude within a first range may be filtered from digital magnetometer output signals having a magnitude within a second range.

When executing one of the applications on the mobile device 1300, the relevant information (i.e., derived from the relevant magnetic source) is provided to that application. In various embodiments, a processor from the mobiles device determines what information is to be made accessible to which application. In some embodiments, the processor may filter the digital magnetometer output signals based on the magnitude of the signals detected by the magnetometer (also referred to as digital magnetometer output signals). In some examples, the magnitude range of the signals may be used for filtering. In other embodiments, a processor in another computing device or component may be used to perform the filtering of the output signals produced by the magnetometer based on the magnitude of the output signals.

In some embodiments, the networked system 102 includes one or more remote servers and associated databases. The client applications installed in the mobile device 1300 may have a corresponding server-side application hosted by the networked system 102. For example, the compass applications 1620 (corresponding to the compass applications 1320), the magnetic swipe card applications 1630 (corresponding to the magnetic swipe card applications 1330), and the other magnetic applications 1640 (corresponding to the other magnetic applications 1340) may be hosted by the networked system 102. In some embodiments the functional components of an application may be shared or distributed between the client application and the corresponding server-side application. For example, the mobile device 1300, which includes the magnetometer 1310, may sense and capture the magnetic signals from or more sources, and the processing (e.g., filtering, processing, and actions based on the various signals) could be performed partially by the networked system 102, or partially by the networked system 102.

In one example embodiment, a mobile device comprises a housing having an integrated surface for swiping a magnetic swipe card; a magnetometer, positioned within the mobile device, for detecting direction and strength of magnetic fields to read magnetic information and to produce digital magnetometer output signals. The digital magnetometer output signals representing magnetic information derived from the magnetic swipe card and from the Earth's magnetic fields. Each of the digital magnetometer output signals having a magnitude related to the strength of the detected magnetic fields. The mobile devices comprises a memory device for storing instructions and a processor coupled to the magnetometer, when executing the instructions, causes the mobile device to: determine at least some of the digital magnetometer output signals represent the magnetic information derived from the magnetic card information; determine at least some of the digital magnetometer output signals represent the magnetic information derived from the Earth's magnetic fields; provide the digital magnetometer output signals representing the magnetic information derived from the magnetic card information to a magnetic swipe card application for processing; and provide the digital magnetometer output signals representing the magnetic information derived from the Earth's magnetic information to a compass application for processing.

The mobile device 1300 includes a magnetometer 1310 which is used to measure magnetic fields. Generally, a magnetometer includes a sensor that measures magnetic flux density B (in units of tesla). Magnetic fields are considered vector quantities characterized by both strength and direction. The strength of a magnetic field is measured in units of tesla in the international system of units (SI units), and in gauss in the centimeter-gram-second system of units (cgs units). 10,000 gauss are equal to one tesla. Measurements of the Earth's magnetic field are often quoted in units of nanotesla (nT), also called a gamma. The Earth's magnetic field can vary from 20,000 to 80,000 nT depending on location, fluctuations in the Earth's magnetic field are on the order of 100 nT, and magnetic field variations due to various magnetic anomalies in the picotesla (pT) range.

There are two basic types of magnetometer measurements. Vector magnetometers measure the vector components of a magnetic field. Total field magnetometers or scalar magnetometers measure the magnitude of the vector magnetic field. Magnetometers used to study the Earth's magnetic field may express the vector components of the field in terms of declination (the angle between the horizontal component of the field vector and magnetic north) and the inclination (the angle between the field vector and the horizontal surface).

Many smartphones available today contain magnetometers that detect magnetic information that are provided to applications that serve as compasses. For example, the magnetometer in the iPhone® (manufactured by Apple® Inc.) provides the magnetic field strength along three axis in micro-teslas (µT) and can be used to find the direction the iPhone® is pointed in. The magnetometers in the iPhone® can also be used to measure the strength of magnetic fields. In some iPhones®, the magnetometer is implemented using an AK8973 chip or AK8963 chip (manufactured by Asahi Kasei MicroDevices Corp.) to detect magnetic fields using the Hall effect. These chips are 3-axis electronic compass integrated circuits (IC) with high sensitivity Hall sensor technology. Example iPhones® can measure magnetic fields up to about 1 T with a precision of about 8 µT (8 microteslas).

Magnetic saturation and remanence are two characteristics that determine the strength (or measurability) of the magnetic information provided by magnetic swipe card information. The magnetic saturation represents the maximum magnetization a stripe can carry and the point at which it produces its highest output signal amplitude. The remanence represents the extent the stripe remains magnetized after having applied the saturating magnetic field. There is a third characteristic, coercivity, which determines how much magnetic field it takes to erase or overwrite a magnetic stripe. Low-coercivity cards are around 300 Oersted (Oed) (30,000 micro-Teslas), while high-coercivity cards are around 4000 Oed (400.000 micro-Teslas). In example embodiments, the coercivity of the magnetic stripes used in cards falls somewhere between 300-4000 Oed.

As described above, a magnetic swipe card 1200 is a type of card capable of storing data by modifying the magnetism of tiny iron-based magnetic particles on a band of magnetic material on the card. FIG. 2 illustrates a magnetic swipe card 1200 according to an example embodiment. By encoding data on the magnetic stripe, data can be entered into a computer with a single swipe of the magnetic swipe card 1200. The dimensions shown in FIG. 2 represent the dimension of an example financial transaction card. The dimensions of an example magnetic swipe card 1200 includes a thickness 203 of 0.030 inches, a height 201 of 2.125 inches, and a width 202 of 3.375 inches. Other magnetic swipe cards may have different dimensions.

In most magnetic swipe cards (e.g., the magnetic swipe card 1200) is contained in a plastic-like film. The magnetic stripe 204 is located 0.223 inches (5.66 mm) from the edge of the card. The magnetic stripe contains three tracks, each 0.110 inches (2.79 mm) wide. Tracks one and three are typically recorded at 210 bits per inch (8.27 bits per mm), while track two typically has a recording density of 75 bits per inch (2.95 bits per mm). Each track can either contain 7-bit alphanumeric characters, or 5-bit numeric characters. Track 1 standards were created by the airlines industry (IATA). Track 2 standards were created by the banking industry (ABA). Track 3 standards were created by the Thrift-Savings industry.

Currently, there are many standards by the International Organization for Standardization and by the International Electrotechnical Commission referred to as ISO/IEC standards for magnetic stripe use. The most commonly used standards are the ISO/IEC 7810, 7811, 7812 and 7813 series of standards. These standards are written for the credit and debit card market and so include information on the embossed characters on the cards as well as the track locations and information on the magnetic stripe. ISO/IEC 7811 has six parts with parts two and six specifically about low and high coercivity magnetic stripes. These standards include information on the magnetic properties that guarantee that the stripe can be read in a magnetic stripe reader in the U.S.A. as well as in Japan. The ISO/IEC 7811 series of standards define track one as a read only track with 210 bits per inch and 6 bits plus a parity bit per character. This allows for a full alpha-numeric encoding. Track two and three both use four bits plus a parity bit (number characters plus A to F) only, with track two at 75 bits per inch and track three at 210 bits per inch. Additionally, three new American National Standards (ANSI) standards that relate to magnetic stripe performance are in progress. These are: (1) Effective Magnetic Parameters of Magnetic Stripes; (2) Suggested Magnetic Parameter Values for Applications; and (3) Magnetic Stripe Readers and Encoders—Equipment Specifications.

Magnetic stripe technology is used by many people and often on a daily basis in various industries. The transportation industry often uses the stripe technology for airline tickets and other transportation or transit tickets. The security industry often uses the magnetic stripe technology on security badges and security checkpoints. The retail industry often uses the stripe technology on loyalty cards and reward cards. The financial industry often uses the stripe technology on financial transaction cards (e.g., credit cards, debit cards, and other banking cards). Today, financial cards (which generally adhere to the ISO standards to ensure read reliability world-wide) and along with transportation cards constitute the largest users of magnetic swipe cards.

Magnetic stripe technology provides an optimal solution to many aspects of our lives. It is very inexpensive and readily adaptable to many functions. The standardization of high coercivity for the financial markets has provided the industry with an extended life. This coupled with the advent of the security techniques now available means that many applications can expect to be using magnetic stripe technology in the future.

Examples of cards adhering to these standards include ATM cards, bank cards (credit and debit cards including VISA and MasterCard), gift cards, loyalty cards, driver's licenses, telephone cards, membership cards, electronic benefit transfer cards (e.g. food stamps), and nearly any application in which value or secure information is not stored on the card itself. Many video game and amusement centers now use debit card systems based on magnetic swipe cards.

Figure 3A:
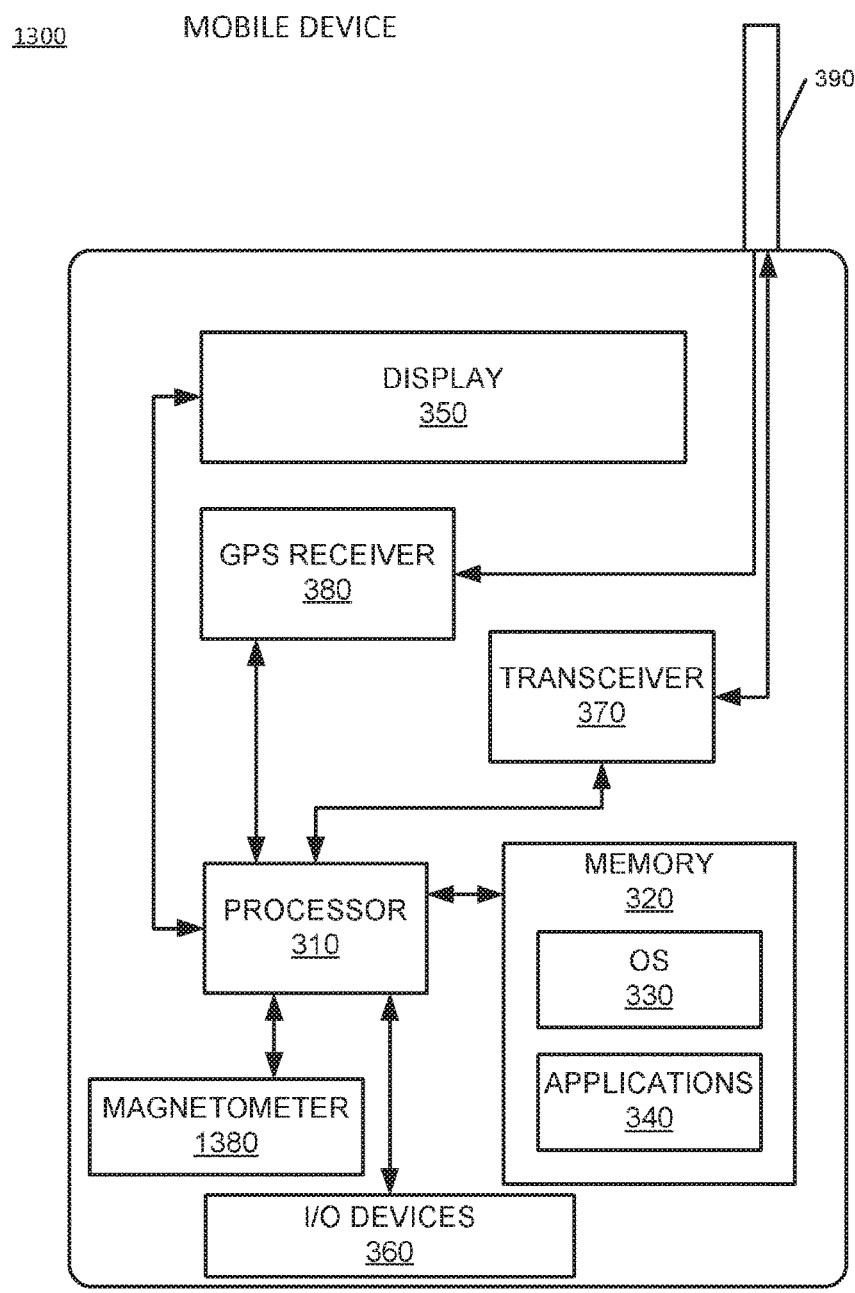
FIGS. 3A-3B illustrate a mobile device that includes a magnetometer for reading magnetic information, according to an example embodiment.

FIG. 3A is a block diagram of a mobile device 1300, according to an example embodiment. In some embodiments, the mobile device 1300 may be a smartphone, and in alternative embodiments, the mobile device 1300 may be a tablet computer, personal computer, laptop computer, netbook, set-top box, video game console, head-mounted display (HMD) or other wearable computing device, other types of devices that includes a magnetometer. The mobile device 1300 may include a processor 310, which may be any of a variety of different types of commercially available processors suitable for mobile devices (for example, an XScale architecture microprocessor, a Microprocessor without Interlocked Pipeline Stages (MIPS) architecture processor, or another type of processor). In example embodiments, the processor 310 may be implemented with one or more central processing units (CPUs), micro-controllers, graphics processing units (GPUs) and/or digital signal processors (DSPs).

A memory 320, such as a Random Access Memory (RAM), a Flash memory, or another type of memory, is typically accessible to the processor 310. The memory 320 may be adapted to store an operating system (OS) 330, as well as applications 340. The applications 340 may represent the compass applications 1320, the magnetic swipe card applications 1330, and other magnetic applications 1340.

The processor 310 may be coupled, either directly or via appropriate intermediary hardware, to a display 350 and to one or more input/output (I/O) devices 360, such as a keypad, a touch panel sensor, a microphone and the like. Additionally, the mobile device 1300 may include a magnetometer 1310.

The performance and capabilities of magnetometers (e.g., magnetometer 1310) are described through their technical specifications. Major specifications include:

Sample rate is the number of readings given per second. The inverse is the cycle time in seconds per reading. Sample rate is important in mobile magnetometers; the sample rate and the vehicle speed determine the distance between measurements.

Bandwidth or bandpass characterizes how well a magnetometer tracks rapid changes in magnetic field. For magnetometers with no onboard signal processing, bandwidth is determined by the Nyquist limit set by sample rate. Modem magnetometers may perform smoothing or averaging over sequential samples achieving a lower noise in exchange for lower bandwidth Resolution is the smallest change in magnetic field the magnetometer can resolve. A magnetometer should have a resolution a good deal smaller than the smallest change one wishes to observe, to avoid quantization errors.

Absolute error is the difference between the averaged readings of a magnetometer in a constant magnetic field and true magnetic field.

Drift is the change in absolute error over time.

Thermal stability is the dependence of the measurement on temperature. It is given as a temperature coefficient in units of nT per degree Celsius.

Noise is the random fluctuations generated by the magnetometer sensor or electronics. Noise is given in units of $nT/\sqrt{Hz}$, where frequency component refers to the bandwidth.

Sensitivity is the larger of the noise or the resolution.

Heading error is the change in the measurement due to a change in orientation of the instrument in a constant magnetic field.

The dead zone is the angular region of magnetometer orientation in which the instrument produces poor or no measurements. All optically pumped, proton-free precession, and Overhauser magnetometers experience some dead zone effects.

Gradient tolerance is the ability of a magnetometer to obtain a reliable measurement in the presence of a magnetic field gradient.

Similarly, in some embodiments, the processor 310 may be coupled to a transceiver 370 that interfaces with an antenna 390. The transceiver 370 may be configured to both transmit and receive cellular network signals, wireless data signals, or other types of signals via the antenna 390, depending on the nature of the mobile device 1300. In this manner, a connection between the mobile device 1300 and the network 104 may be established. Further, in some configurations, a GPS receiver 380 may also make use of the antenna 390 to receive GPS signals.

Figure 3B:
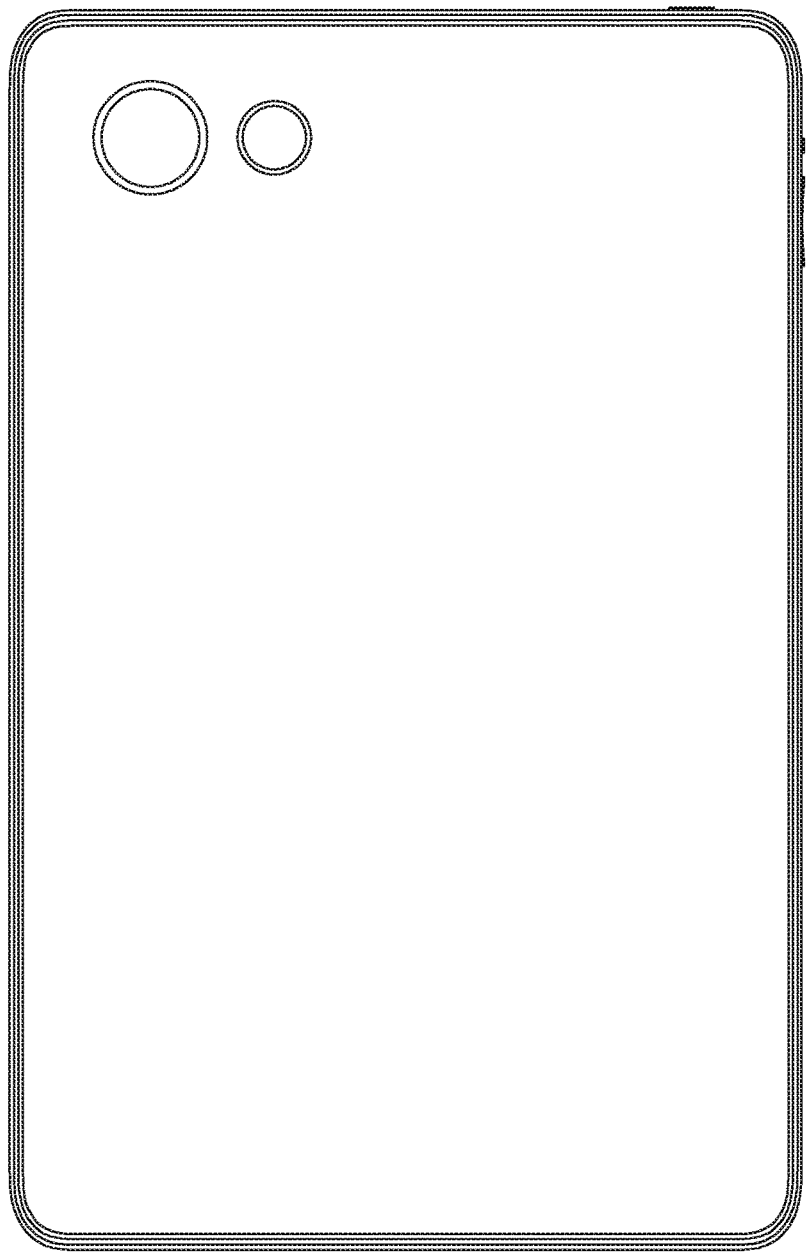

FIG. 3B illustrates a back view 1320 of the mobile device 1300 according to an example embodiment. In various embodiments, the back view represents a back surface of the mobile device 1300 that may be used as a swiping surface for the magnetic swipe card 1200.

Figure 4:
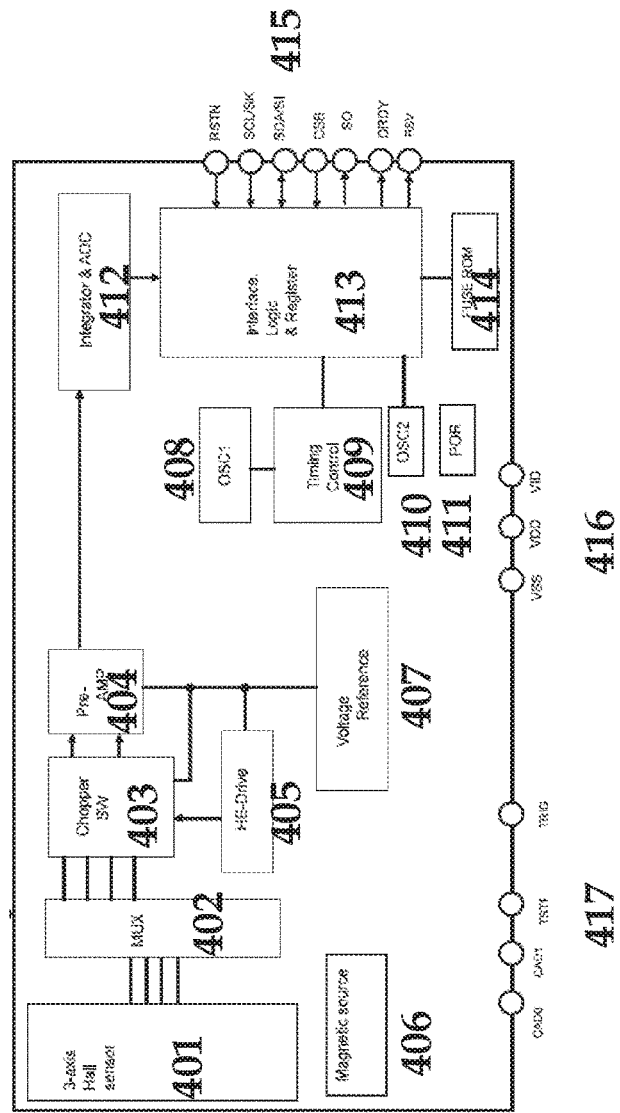
FIG. 4 illustrates an electronic compass integrated circuit, according to an example embodiment.

FIG. 4 illustrates an electronic compass IC 400 according to an example embodiment. In some embodiments the magnetometer 1310 (shown in FIG. 1) may be implemented using an integrated circuit compass chip such as the electronic compass IC 400 located within the mobile device 1300 (shown in FIG. 1). The electronic compass IC 400 may detect and capture magnetic signals, and in some embodiments, may perform additional processing of the magnetic sensor signals. The electronic compass IC 400 may be implemented using the AK8963 IC which incorporates magnetic sensors for detecting terrestrial magnetism in the X-axis, Y-axis, and Z-axis, a sensor driver circuit, a signal amplifier chain, and an arithmetic circuit for processing the magnetic sensor signal from each sensor. The AK8963 chip includes a wide dynamic measurement range and high resolution with lower current consumption. Output data resolution: 14-bit (0.6 uT/LSB) and 16-bit (0.15 uT/LSB).

In some embodiments, one or more hardware and/or software components within the electronic compass IC circuit 400 may need to modified (or new components added) to detect and measure the magnetic fields from the desired magnetic sources. For example, the sensitivity of the electronic compass IC circuit 400 may need to be increased to read and process the magnetic card information from a magnetic swipe card or the medical information from a human body.

The electronic compass IC circuit 400 includes a 3-axis Hall sensor 401 that includes monolithic Hall elements; a MUX 402 for selecting Hall elements; a chopper SW 403 that performs chopping (i.e., breaking up DC signals so it can be processed more easily and amplified, increasing stability and accuracy of the signal); a HE-Drive 405 representing a magnetic sensor drive circuit, a pre-amp 404 representing a fixed-gain differential amplifier used to amplify the magnetic sensor signal; a voltage reference 407; an integrator & ADC 412 that integrates and amplifies the pre-AMP output and performs analog-to-digital conversion, an interface logic & register 413 that exchanges signals with a CPU using input/outputs (I/Os) 415; an OSC1 408 generates an operating clock for sensor measurement; an OSC2 410 generates an operating clock for sequencer; timing control 409 generates a timing signal required for internal operation from a clock generated by the OSC1 408; a POR 411 representing a power on reset circuit; a fuse ROM 414 representing a fuse for adjustment; a magnetic source 406 generates a magnetic field for self-test of a magnetic sensor. Various power supply pins 415 include pins VSS, VDD and VID. Various input current pins 417 include pins CAD0, CAD1, TRG and TST1. The chopper 403 is an electronic switch that interrupts a signal under the control of another; and corrects for signal errors, in this case, resulting from the Hall effect. The I/Os 415 include an SDA/SI terminal for receiving input signals and an SO terminal for providing output signals via a digital serial interface (e.g., $I^2C$ bus interface).

Figure 5:
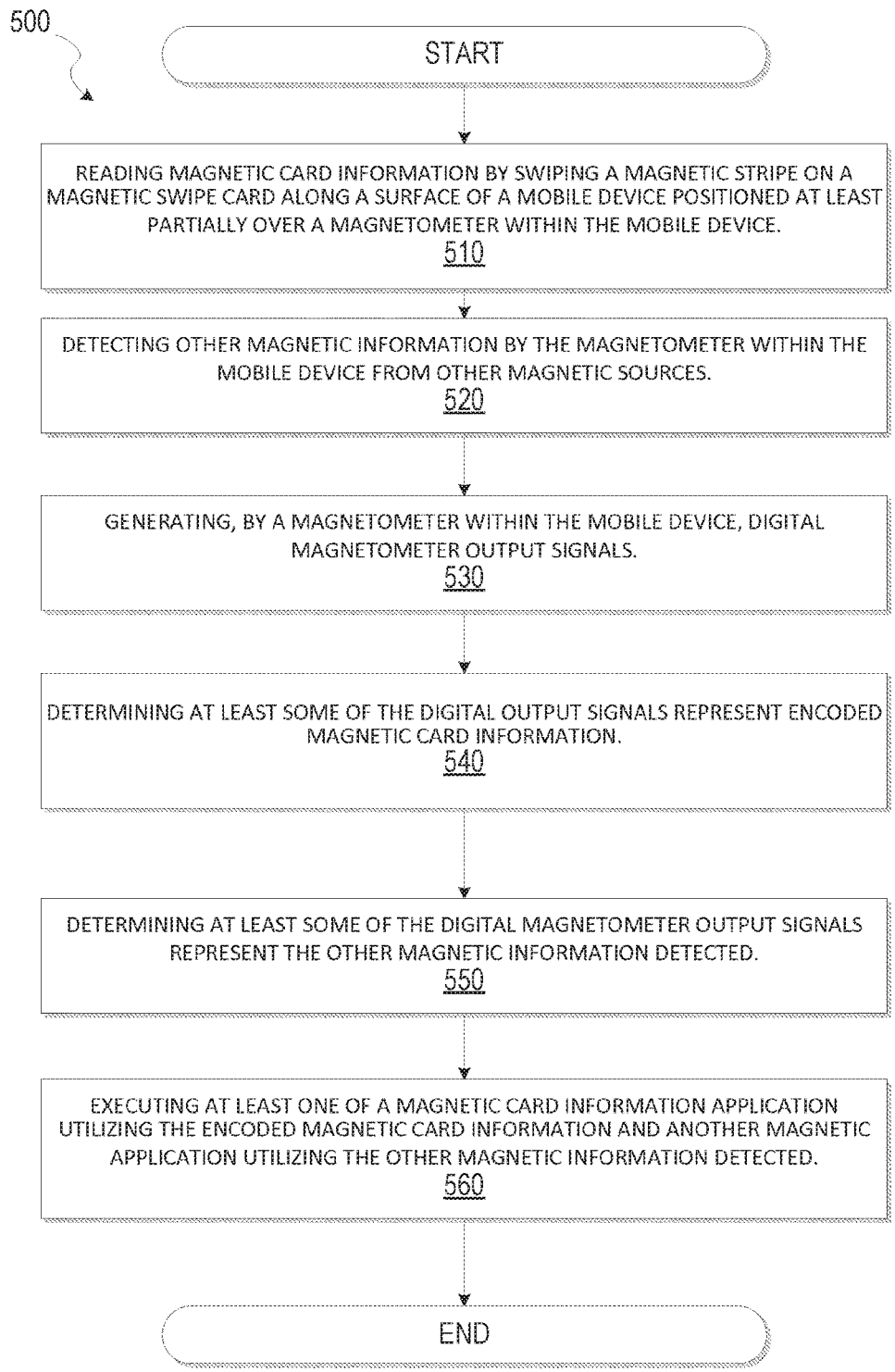
FIG. 5 illustrates a flow diagram of a method for detecting magnetic card information from a magnetic card reader, according to an example embodiment.
Figure 6:
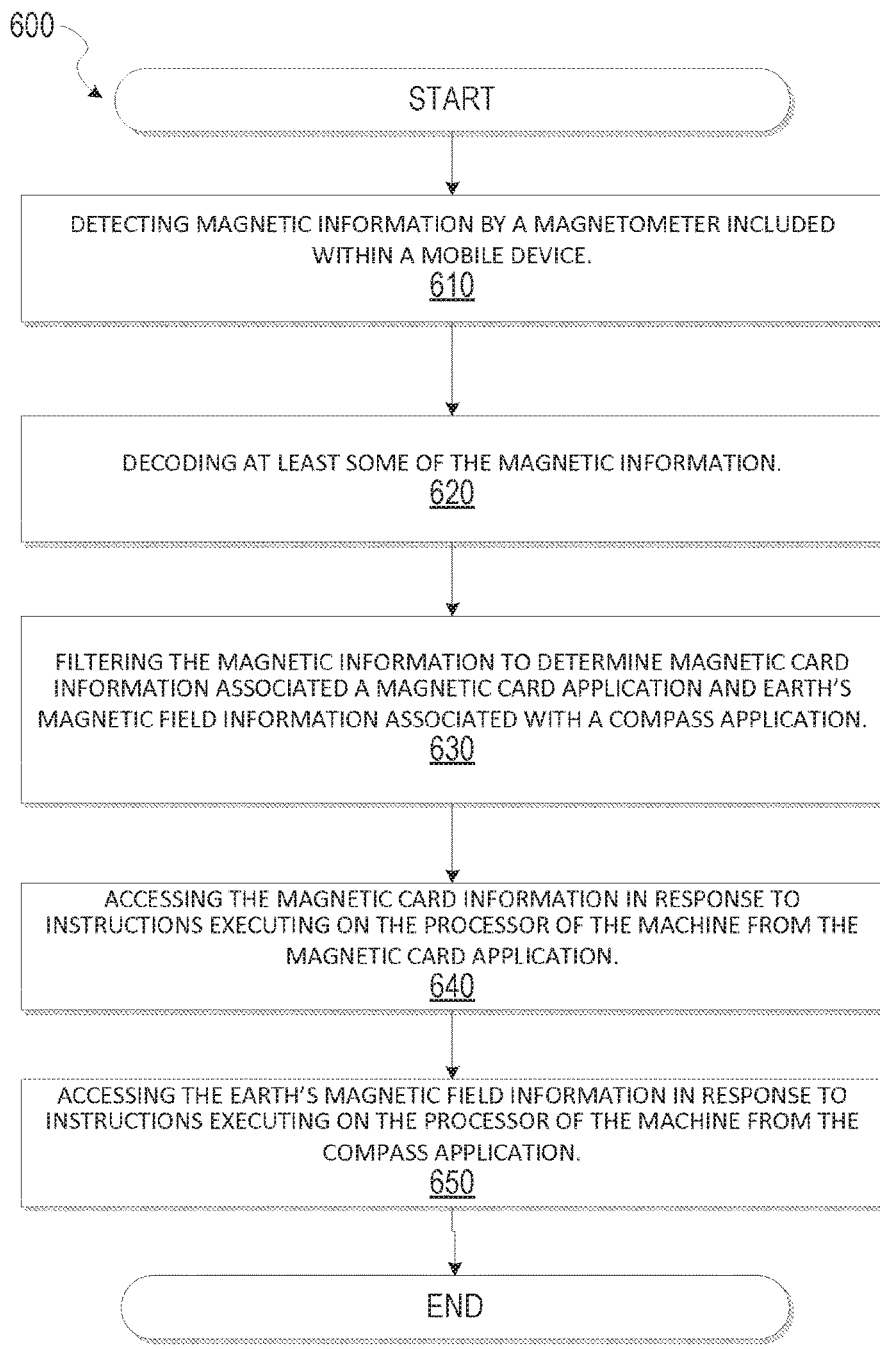
FIG. 6 illustrates a flow diagram of a method for detecting magnetic card information from a magnetic card reader, according to another example embodiment.

FIGS. 5-6 illustrates flow diagrams for methods 500-600 implemented in various embodiments. In some embodiments, additional operations may be added to each of the methods 500-600, or one or more operations may be deleted from each of the methods 500-600. In further embodiments, the methods 500-600 or variants of these methods, may be combined. The operations performed in the methods 500-600 may be performed by one or more components or modules within the networked system 102 (e.g., magnetic reader system 750) or by the mobile device 1300. For example, some of the operations performed by the methods 500-600 may be executed by the magnetic swipe card application 1630 running on the networked system 102, or the magnetic swipe card application 1320 running on the mobile device 1300. For example, the reading of the magnetic information from the various magnetic sources may occur at a mobile device, but further processing of the signals detected by the magnetometer may be performed by the mobile device or other computing device (e.g., a remote server).

FIG. 5 describes a method 500 for reading and detecting digital magnetometer output signals for utilization by various applications, according to example embodiments. The method 500 includes operations 510-560. At operation 510, magnetic card information is ready by swiping a magnetic stripe on a magnetic swipe card along a surface of a mobile device positioned at least partially over a magnetometer within the mobile device.

At operation 520, other magnetic information is detected by the magnetometer within the mobile device from other magnetic sources. For example, other magnetic information sensed by a magnetometer (e.g., magnetometer 1310) may include, for example, magnetic information related to the Earth's magnetic fields, magnetic information related to a user or human body, magnetic information related to electronic components, or magnetic information related to other items in the environment.

At operation 530, generating, by a magnetometer within the mobile device, digital magnetometer output signals. At operation 540, determining, by a processor of a machine, at least some of the digital magnetometer output signals represent encoded magnetic card information. At operation 550, determining, by a processor of a machine, at least some of the digital magnetometer output signals represent the other magnetic information detected. At operation 560, executing, by a processor of a machine, at least one of a magnetic card information application utilizing the encoded magnetic card information and another magnetic application utilizing the other magnetic information detected.

In other embodiments, the method 500 includes: storing the digital magnetometer output signals; accessing, by the processor of the machine, the encoded magnetic card information based on instructions from the magnetic card information application; and accessing, by the processor of the machine, the other magnetic application based on instructions from the other magnetic application.

In another embodiment, the operation of determining at least some of the digital magnetometer output signals represent encoded magnetic card information includes identifying the encoded magnetic card information based on the strength of the magnetic fields generated by magnetic stripe on the magnetic swipe card.

In a further embodiment, the operation of determining at least some of the digital magnetometer output signals represent the detected other magnetic information includes identifying the other magnetic information based on the strength of the magnetic fields generated by the Earth.

In yet another embodiment, the operation of determining at least some of the digital magnetometer output signals represent the detected other magnetic information includes identifying the other magnetic information based on the strength of the magnetic fields generated by a blood sample.

In an example embodiment, a method for reading and detecting digital magnetometer output signals for utilization by various applications, includes the operations of: detecting, by a magnetometer within a mobile device, direction and strength of magnetic fields from a magnetic swipe card that were swiped along a surface of the mobile device; detecting, by the magnetometer within the mobile device, direction and strength of magnetic fields from an other magnetic source; generating, by the magnetometer within the mobile device, digital magnetometer output signals, the digital magnetometer output signals representing magnetic information derived from the magnetic swipe card and from the other magnetic source, each of the digital magnetometer output signals having a magnitude related to the strength of the detected magnetic fields; determining, by a processor of a machine, at least some of the digital magnetometer output signals represent the detected magnetic information derived from the magnetic swipe card; determining, by a processor of a machine, at least some of the digital magnetometer output signals represent the detected magnetic information from the other magnetic source; and executing, by a processor of a machine, at least one of a magnetic card application utilizing the digital magnetometer output signals representing the detected magnetic information derived from the magnetic swipe card and an other application utilizing the digital magnetometer output signals representing the detected magnetic information derived the other magnetic source.

FIG. 6 describes a method 600 for detecting digital magnetometer output signals for utilization by various applications, according to example embodiments. The method 600 includes operations 610-650. At operation 610, detecting magnetic information by a magnetometer included within a mobile device. At operation 620, decoding, by a processor of a machine, at least some of the magnetic information that was detected to produce an output signal.

At operation 630, filtering, by a processor of a machine, the magnetic information to determine magnetic card information associated a magnetic card application and Earth's magnetic field information associated with a compass application. More specifically, filtering the magnetic information derived from various sources based on magnitudes of the output signals. For example, the magnetic card information has output signals with magnitudes within a first range and the Earth's magnetic field information has output signals with magnitudes within a second range.

At operation 640, accessing the magnetic card information in response to instructions executing on the processor of the machine from the magnetic card application. At operation 650 accessing the Earth's magnetic field information in response to instructions executing on the processor of the machine from the compass application.

In another embodiment, the method 600 includes filtering, by the processor of the machine, the magnetic information to determine medical information associated with a medical application; and accessing the medical information in response to instructions executing on the processor of the machine from a medical application.

In an example embodiment, a method for reading and detecting digital magnetometer output signals for utilization by various applications, includes the operations of receiving digital magnetometer output signals captured by a mobile device, the digital magnetometer output signals including magnetic information derived from a magnetic swipe card and Earth's magnetic field; filtering the magnetic information to determine whether the digital magnetometer output signals represents magnetic information associated with the magnetic swipe card or magnetic information associated with the Earth's magnetic fields based on a magnitude of the digital magnetometer output signals; providing the digital magnetometer output signals representing the magnetic information associated with the magnetic swipe card to a magnetic swipe card application for processing; and providing the digital magnetometer output signals representing the magnetic information associated with the Earth's magnetic fields to a compass application for processing.

With reference to FIG. 7, an example embodiment of a high-level client-server-based network architecture 700 is shown. A networked system 102, in the example forms of a network-based marketplace or payment system, provides server-side functionality via a network 104 (e.g., the Internet or wide area network (WAN)) to one or more client devices 710. FIG. 7 illustrates, for example, a web client 712 (e.g., a browser, such as the Internet Explorer® browser developed by Microsoft® Corporation of Redmond, Wash. State), client application(s) 714, and a programmatic client 716 executing on client device 710.

The client device 710 may comprise, but are not limited to, a mobile phone, or other client devices that include a magnetometer. For example, desktop computer, laptop, portable digital assistants (PDAs), smart phones, tablets, ultra books, netbooks, laptops, multi-processor systems, microprocessor-based or programmable consumer electronics, game consoles, set-top boxes, or any other device that may access the networked system 102 may include a magnetometer. In various embodiments, a mobile device, includes one or more devices described above, that has a magnetometer capable of measuring the strength of magnetic fields from a variety of sources. In some embodiments, the client device 710 may comprise a display module (not shown) to display information (e.g., in the form of user interfaces). In further embodiments, the client device 710 may include one or more of a magnetometer or other magnetic reader, touch screens, accelerometers, gyroscopes, cameras, microphones, global positioning system (GPS) devices, and so forth. The client device 710 may be a device of a user that is used to perform a transaction involving digital items within the networked system 102. In one embodiment, the networked system 102 is a network-based marketplace that responds to requests for product listings, publishes publications comprising item listings of products available on the network-based marketplace, and manages payments for these marketplace transactions. One or more users 706 may be a person, a machine, or other means of interacting with client device 710. In embodiments, the user 706 is not part of the network architecture 700, but may interact with the network architecture 700 via client device 710 or another means. For example, one or more portions of network 104 may be an ad hoc network, an intranet, an extranet, a virtual private network (VPN), a local area network (LAN), a wireless LAN (WLAN), a wide area network (WAN), a wireless WAN (WWAN), a metropolitan area network (MAN), a portion of the Internet, a portion of the Public Switched Telephone Network (PSTN), a cellular telephone network, a wireless network, a Wi-Fi network, a WiMAX network, another type of network, or a combination of two or more such networks.

Each of the client device 710 may include one or more applications (also referred to as "apps") such as, but not limited to, a web browser, messaging application, electronic mail (email) application, an e-commerce site application (also referred to as a marketplace application), and the like. In some embodiments, if the e-commerce site application is included in a given one of the client device 710, then this application is configured to locally provide the user interface and at least some of the functionalities with the application configured to communicate with the networked system 102, on an as needed basis, for data and/or processing capabilities not locally available (e.g., access to a database of items available for sale, to authenticate a user, to verify a method of payment, etc.). Conversely if the e-commerce site application is not included in the client device 710, the client device 710 may use its web browser to access the e-commerce site (or a variant thereof) hosted on the networked system 102.

One or more users 706 may be a person, a machine, or other means of interacting with the client device 710. In example embodiments, the user 706 is not part of the network architecture 700, but may interact with the network architecture 700 via the client device 710 or other means. For instance, the user provides input (e.g., touch screen input or alphanumeric input) to the client device 710 and the input is communicated to the networked system 102 via the network 104. In this instance, the networked system 102, in response to receiving the input from the user, communicates information to the client device 710 via the network 104 to be presented to the user. In this way, the user can interact with the networked system 102 using the client device 710.

An application program interface (API) server 720 and a web server 722 are coupled to, and provide programmatic and web interfaces respectively to, one or more application server(s) 740. The application servers 740 may host one or more publication systems 742 and payment systems 744, each of which may comprise one or more modules or applications and each of which may be embodied as hardware, software, firmware, or any combination thereof. The application servers 740 are, in turn, shown to be coupled to one or more database server(s) 724 that facilitate access to one or more information storage repositories or database(s) 726. In an example embodiment, the database(s) 726 are storage devices that store information to be posted (e.g., publications or listings) to the publication system 720. The database(s) 726 may also store digital item information in accordance with example embodiments.

Additionally, a third party application 732, executing on third party server(s) 730, is shown as having programmatic access to the networked system 102 via the programmatic interface provided by the API server 720. For example, the third party application 732, utilizing information retrieved from the networked system 102, supports one or more features or functions on a website hosted by the third party. The third party website, for example, provides one or more promotional, marketplace, or payment functions that are supported by the relevant applications of the networked system 102.

The publication systems 742 may provide a number of publication functions and services to users 706 that access the networked system 102. The payment systems 744 may likewise provide a number of functions to perform or facilitate payments and transactions. While the publication system 742 and payment system 744 are shown in FIG. 7 to both form part of the networked system 102, it will be appreciated that, in alternative embodiments, each system 742 and 744 may form part of a payment service that is separate and distinct from the networked system 102. In some embodiments, the payment systems 744 may form part of the publication system 742.

The magnetic reader system 750 may provide functionality operable to execute various applications utilizing information from various magnetic sources. In an example embodiment, the onboard processing performed using the mobile device 1300 (shown in FIG. 1) and the signal capture processing is performed by the magnetic reader system 750. For example, the filtering, processing, and actions based on the various signals could be determined by the application server(s) 740 (e.g., the magnetic reader system 750), and therefore making the client device 710 more of a thin client which is used only for sensing and capturing the signals from the magnetic sources. In other example embodiments, the onboard processing and the signal capture processing is performed by the client device 710 (e.g., mobile device 1300).

For example, the magnetic reader system 750 may access the user selected data from the databases 726, the third party servers 730, the publication system 742, and other sources. In some example embodiments, the magnetic reader system 750 may execute some or all of the components of at least one of the compass applications 1620, the magnetic swipe card applications 1630, and the other magnetic applications 1640.

In some example embodiments, the magnetic reader system 750 may communicate with the publication system(s) 742 and payment system(s) 744. For example, when the source of the magnetic information is derived from a financial transaction card, the magnetic reader system 750 may communicate with the payment system(s) 744. In other embodiments, when the source of the magnetic information is derived from a rewards card or a loyalty card, the magnetic reader system 750 may communicate with the publication systems 120. In an alternative embodiment, the magnetic reader system 750 may be a part of at least one of the publication system 742 and the payment system 744.

Further, while the client-server-based network architecture 700 shown in FIG. 7 employs a client-server architecture, the present inventive subject matter is of course not limited to such an architecture, and could equally well find application in a distributed, or peer-to-peer, architecture system, for example. The various publication system 742, payment system 744, and magnetic reader system 750 could also be implemented as standalone software programs, which do not necessarily have networking capabilities.

The web client 712 may access the various publication and payment systems 742 and 744 via the web interface supported by the web server 722. Similarly, the programmatic client 716 accesses the various services and functions provided by the publication and payment systems 742 and 744 via the programmatic interface provided by the API server 720. The programmatic client 716 may, for example, be a seller application (e.g., the Turbo Lister application developed by eBay® Inc., of San Jose, Calif.) to enable sellers to author and manage listings on the networked system 102 in an off-line manner, and to perform batch-mode communications between the programmatic client 716 and the networked system 102.

Additionally, a third party application 732, executing on a third party server(s) 730, is shown as having programmatic access to the networked system 102 via the programmatic interface provided by the API server 720. For example, the third party application 732, utilizing information retrieved from the networked system 102, may support one or more features or functions on a website hosted by the third party. The third party website may, for example, provide one or more promotional, marketplace, or payment functions that are supported by the relevant applications of the networked system 102.

Modules, Components, and Logic

Certain embodiments are described herein as including logic or a number of components, modules, or mechanisms. Modules may constitute either software modules (e.g., code embodied on a machine-readable medium) or hardware modules. A "hardware module" is a tangible unit capable of performing certain operations and may be configured or arranged in a certain physical manner. In various example embodiments, one or more computer systems (e.g., a standalone computer system, a client computer system, or a server computer system) or one or more hardware modules of a computer system (e.g., a processor or a group of processors) may be configured by software (e.g., an application or application portion) as a hardware module that operates to perform certain operations as described herein.

In some embodiments, a hardware module may be implemented mechanically, electronically, or any suitable combination thereof. For example, a hardware module may include dedicated circuitry or logic that is permanently configured to perform certain operations. For example, a hardware module may be a special-purpose processor, such as a Field-Programmable Gate Array (FPGA) or an Application Specific Integrated Circuit (ASIC). A hardware module may also include programmable logic or circuitry that is temporarily configured by software to perform certain operations. For example, a hardware module may include software executed by a general-purpose processor or other programmable processor. Once configured by such software, hardware modules become specific machines (or specific components of a machine) uniquely tailored to perform the configured functions and are no longer general-purpose processors. It will be appreciated that the decision to implement a hardware module mechanically, in dedicated and permanently configured circuitry, or in temporarily configured circuitry (e.g., configured by software) may be driven by cost and time considerations.

Accordingly, the phrase "hardware module" should be understood to encompass a tangible entity, be that an entity that is physically constructed, permanently configured (e.g., hardwired), or temporarily configured (e.g., programmed) to operate in a certain manner or to perform certain operations described herein. As used herein, "hardware-implemented module" refers to a hardware module. Considering embodiments in which hardware modules are temporarily configured (e.g., programmed), each of the hardware modules need not be configured or instantiated at any one instance in time. For example, where a hardware module comprises a general-purpose processor configured by software to become a special-purpose processor, the general-purpose processor may be configured as respectively different special-purpose processors (e.g., comprising different hardware modules) at different times. Software accordingly configures a particular processor or processors, for example, to constitute a particular hardware module at one instance of time and to constitute a different hardware module at a different instance of time.

Hardware modules can provide information to, and receive information from, other hardware modules. Accordingly, the described hardware modules may be regarded as being communicatively coupled. Where multiple hardware modules exist contemporaneously, communications may be achieved through signal transmission (e.g., over appropriate circuits and buses) between or among two or more of the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices, and can operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions described herein. As used herein, "processor-implemented module" refers to a hardware module implemented using one or more processors.

Similarly, the methods described herein may be at least partially processor-implemented, with a particular processor or processors being an example of hardware. For example, at least some of the operations of a method may be performed by one or more processors or processor-implemented modules. Moreover, the one or more processors may also operate to support performance of the relevant operations in a "cloud computing" environment or as a "software as a service" (SaaS). For example, at least some of the operations may be performed by a group of computers (as examples of machines including processors), with these operations being accessible via a network (e.g., the Internet) and via one or more appropriate interfaces (e.g., an Application Program Interface (API)).

The performance of certain of the operations may be distributed among the processors, not only residing within a single machine, but deployed across a number of machines. In some example embodiments, the processors or processor-implemented modules may be located in a single geographic location (e.g., within a home environment, an office environment, or a server farm). In other example embodiments, the processors or processor-implemented modules may be distributed across a number of geographic locations.

Machine and Software Architecture

The modules, methods, applications and so forth described in conjunction with FIGS. 5-6 are implemented in some embodiments in the context of a machine and an associated software architecture. The sections below describe representative software architecture(s) and machine (e.g., hardware) architecture that are suitable for use with the disclosed embodiments.

Software architectures are used in conjunction with hardware architectures to create devices and machines tailored to particular purposes. For example, a particular hardware architecture coupled with a particular software architecture will create a mobile device, such as a mobile phone, tablet device, or so forth. A slightly different hardware and software architecture may yield a smart device for use in the "internet of things." While yet another combination produces a server computer for use within a cloud computing architecture. Not all combinations of such software and hardware architectures are presented here as those of skill in the art can readily understand how to implement the invention in different contexts from the disclosure contained herein.

Software Architecture

Figure 8:
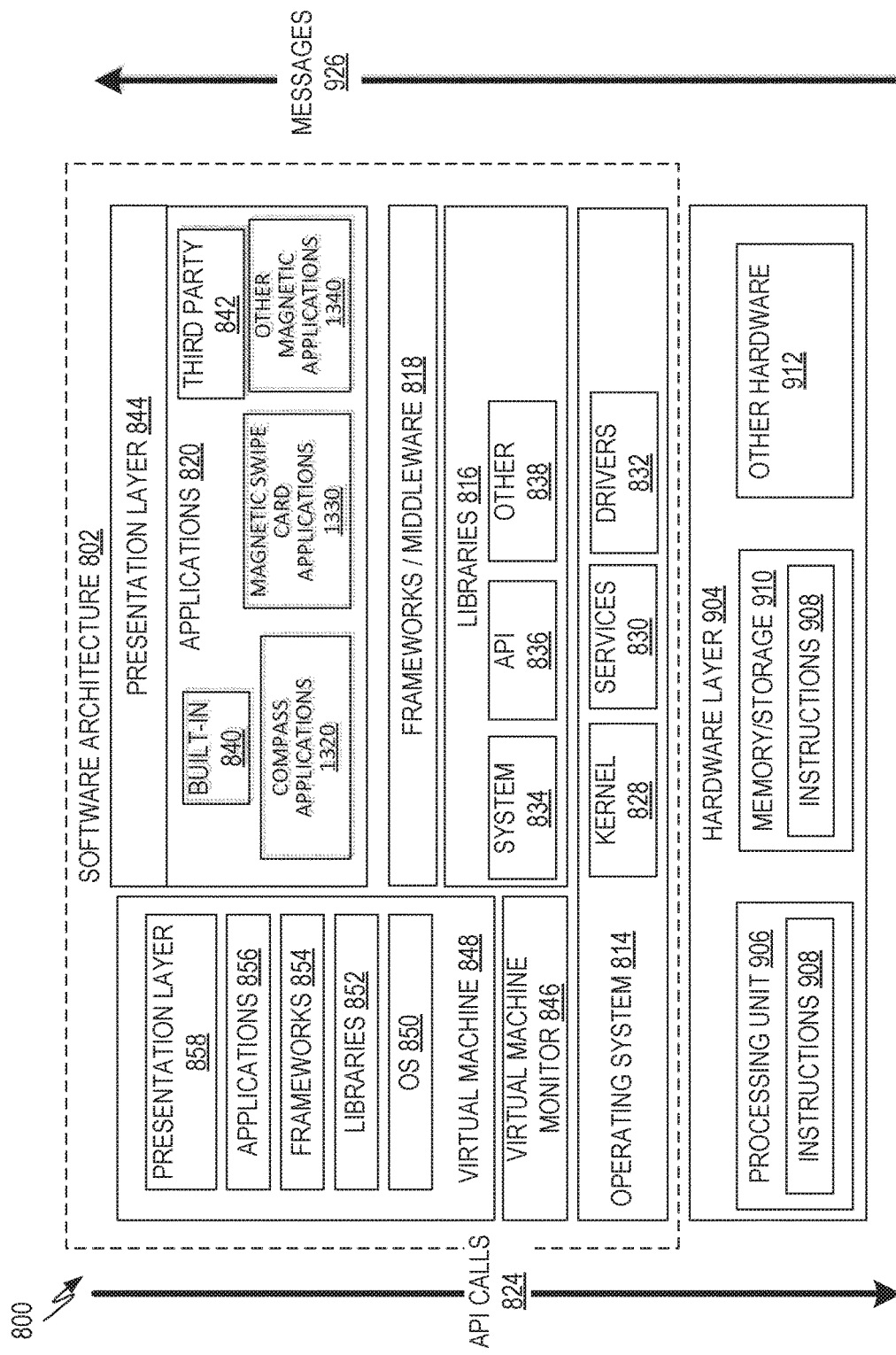
FIG. 8 is a block diagram illustrating an example of a software architecture that may be installed on a machine, according to some example embodiments.

FIG. 8 is a block diagram 800 illustrating a representative software architecture 802, which may be used in conjunction with various hardware architectures herein described. FIG. 8 is merely a non-limiting example of a software architecture and it will be appreciated that many other architectures may be implemented to facilitate the functionality described herein. The software architecture 802 may be executing on hardware such as machine 1000 of FIG. 9 that includes, among other things, processors 1010, memory 1030, and I/O components 1050. A representative hardware layer 904 is illustrated and can represent, for example, the machine 1000 of FIG. 9. The representative hardware layer 904 comprises one or more processing units 906 having associated executable instructions 908. Executable instructions 908 represent the executable instructions of the software architecture 802, including implementation of the methods, modules and so forth of FIGS. 6-7. Hardware layer 904 also includes memory and/or storage modules 910, which also have executable instructions 908. Hardware layer 904 may also comprise other hardware as indicated by 912 which represents any other hardware of the hardware layer 904, such as the other hardware illustrated as part of machine 1000.

In the example architecture of FIG. 8, the software 802 may be conceptualized as a stack of layers where each layer provides particular functionality. For example, the software 802 may include layers such as an operating system 814, libraries 816, frameworks/middleware 818, applications 820 and presentation layer 822. Operationally, the applications 820 and/or other components within the layers may invoke application programming interface (API) calls 824 through the software stack and receive a response, returned values, and so forth illustrated as messages 826 in response to the API calls 824. The layers illustrated are representative in nature and not all software architectures have all layers. For example, some mobile or special purpose operating systems may not provide a frameworks/middleware layer 818, while others may provide such a layer. Other software architectures may include additional or different layers.

The operating system 814 may manage hardware resources and provide common services. The operating system 814 may include, for example, a kernel 828, services 830, and drivers 832. The kernel 828 may act as an abstraction layer between the hardware and the other software layers. For example, the kernel 828 may be responsible for memory management, processor management (e.g., scheduling), component management, networking, security settings, and so on. The services 830 may provide other common services for the other software layers. The drivers 832 may be responsible for controlling or interfacing with the underlying hardware. For instance, the drivers 832 may include display drivers, camera drivers, Bluetooth® drivers, flash memory drivers, serial communication drivers (e.g., Universal Serial Bus (USB) drivers), Wi-Fi® drivers, audio drivers, power management drivers, and so forth depending on the hardware configuration.

The libraries 816 may provide a common infrastructure that may be utilized by the applications 820 and/or other components and/or layers. The libraries 816 typically provide functionality that allows other software modules to perform tasks in an easier fashion than to interface directly with the underlying operating system 814 functionality (e.g., kernel 828, services 830 and/or drivers 832). The libraries 816 may include system 834 libraries (e.g., C standard library) that may provide functions such as memory allocation functions, string manipulation functions, mathematic functions, and the like. In addition, the libraries 816 may include API libraries 836 such as media libraries (e.g., libraries to support presentation and manipulation of various media format such as MPREG4, H.264, MP3, AAC, AMR, JPG, PNG), graphics libraries (e.g., an OpenGL framework that may be used to render 2D and 3D in a graphic content on a display), database libraries (e.g., SQLite that may provide various relational database functions), web libraries (e.g., WebKit that may provide web browsing functionality), and the like. The libraries 816 may also include a wide variety of other libraries 838 to provide many other APIs to the applications 820 and other software components/modules.

The frameworks 818 (also sometimes referred to as middleware) may provide a higher-level common infrastructure that may be utilized by the applications 820 and/or other software components/modules. For example, the frameworks 818 may provide various graphic user interface (GUI) functions, high-level resource management, high-level location services, and so forth. The frameworks 818 may provide a broad spectrum of other APIs that may be utilized by the applications 820 and/or other software components/modules, some of which may be specific to a particular operating system or platform.

The applications 820 includes built-in applications 840 and/or third party applications 842. Examples of representative built-in applications 840 may include, but are not limited to, a contacts application, a browser application, a book reader application, a location application, a media application, a messaging application, and/or a game application. In some embodiments, a compass application and/or a magnetic reader application may be included within the built-in applications 840 and/or third party applications 842. In some embodiments, the magnetic reader application may perform the operations described in methods 500 and 600, shown in FIG. 5 and FIG. 6, respectively. Third party applications 842 may include any of the built in applications as well as a broad assortment of other applications. In a specific example, the third party application 842 (e.g., an application developed using the Android™ or iOS™ software development kit (SDK) by an entity other than the vendor of the particular platform) may be mobile software running on a mobile operating system such as iOS™, Android™, Windows® Phone, or other mobile operating systems. In this example, the third party application 842 may invoke the API calls 824 provided by the mobile operating system such as operating system 814 to facilitate functionality described herein. Examples of other applications included within the applications 820 include the compass applications 1320, the magnetic swipe card applications 1330, and the other magnetic card applications 1340. In other embodiments, the corresponding mobile applications (e.g., the compass applications 1320, the magnetic swipe card applications 1330, and the other magnetic card applications 1340) installed and executable on the mobile device 710 may be included in the client applications 714. In further embodiments, the compass applications, the magnetic swipe card applications, and the other magnetic card applications may be third party applications included within the third party application 842.

The applications 820 may utilize built in operating system functions (e.g., kernel 828, services 830 and/or drivers 832), libraries (e.g., system 834, APIs 836, and other libraries 838), frameworks/middleware 818 to create user interfaces to interact with users of the system. Alternatively, or additionally, in some systems interactions with a user may occur through a presentation layer, such as presentation layer 844. In these systems, the application/module "logic" can be separated from the aspects of the application/module that interact with a user.

Some software architectures utilize virtual machines. In the example of FIG. 8, this is illustrated by virtual machine 848. A virtual machine creates a software environment where applications/modules can execute as if they were executing on a hardware machine (such as the machine of FIG. 9, for example). A virtual machine is hosted by a host operating system (operating system 814 in FIG. 9) and typically, although not always, has a virtual machine monitor 846, which manages the operation of the virtual machine as well as the interface with the host operating system (i.e., operating system 814). A software architecture executes within the virtual machine such as an operating system 850, libraries 852, frameworks/middleware 854, applications 856 and/or presentation layer 858. These layers of software architecture executing within the virtual machine 848 can be the same as corresponding layers previously described or may be different.

Example Machine Architecture and Machine-Readable Medium

Figure 9:
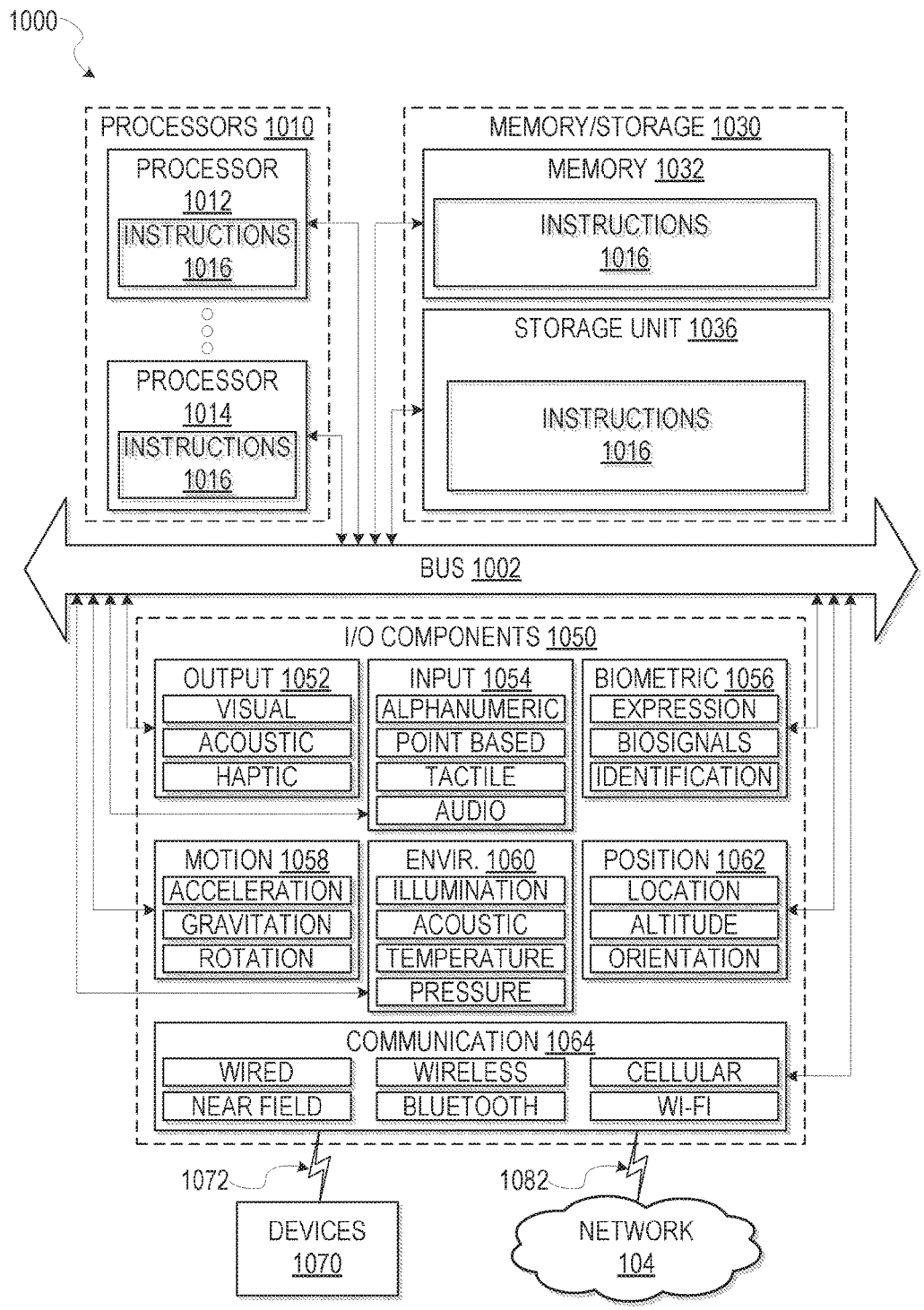
FIG. 9 illustrates a diagrammatic representation of a machine in the form of a computer system within which a set of instructions may be executed for causing the machine to perform any one or more of the methodologies discussed herein, according to an example embodiment.

FIG. 9 is a block diagram illustrating components of a machine 1000, according to some example embodiments, able to read instructions from a machine-readable medium (e.g., a machine-readable storage medium) and perform any one or more of the methodologies discussed herein. Specifically, FIG. 9 shows a diagrammatic representation of the machine 1000 in the example form of a computer system, within which instructions 1016 (e.g., software, a program, an application, an applet, an app, or other executable code) for causing the machine 1000 to perform any one or more of the methodologies discussed herein may be executed. For example the instructions may cause the machine to execute the flow diagrams of FIGS. 5-6. The instructions transform the general, non-programmed machine into a particular machine programmed to carry out the described and illustrated functions in the manner described. In alternative embodiments, the machine 1000 operates as a standalone device or may be coupled (e.g., networked) to other machines. In a networked deployment, the machine 1000 may operate in the capacity of a server machine or a client machine in a server-client network environment, or as a peer machine in a peer-to-peer (or distributed) network environment. The machine 1000 may comprise, but not be limited to, a server computer, a client computer, a personal computer (PC), a tablet computer, a laptop computer, a netbook, a cellular telephone, a smart phone, a mobile device, a wearable device (e.g., a smart watch), a smart home device (e.g., a smart appliance), other smart devices, a web appliance, or any machine capable of executing the instructions 1016, sequentially or otherwise, that specify actions to be taken by machine 1000. In various embodiments, the mobile device refers to one or more of the devices described above that is considered mobile. Further, while only a single machine 1000 is illustrated, the term "machine" shall also be taken to include a collection of machines 1000 that individually or jointly execute the instructions 1016 to perform any one or more of the methodologies discussed herein.

The machine 1000 may include processors 1010, memory 1030, and I/O components 1050, which may be configured to communicate with each other such as via a bus 1002. In an example embodiment, the processors 1010 (e.g., a Central Processing Unit (CPU), a Reduced Instruction Set Computing (RISC) processor, a Complex Instruction Set Computing (CISC) processor, a Graphics Processing Unit (GPU), a Digital Signal Processor (DSP), an Application Specific Integrated Circuit (ASIC), a Radio-Frequency Integrated Circuit (RFIC), another processor, or any suitable combination thereof) may include, for example, processor 1012 and processor 1014 that may execute instructions 1016. The term "processor" is intended to include multi-core processor that may comprise two or more independent processors (sometimes referred to as "cores") that may execute instructions contemporaneously. Although FIG. 9 shows multiple processors, the machine 1000 may include a single processor with a single core, a single processor with multiple cores (e.g., a multi-core process), multiple processors with a single core, multiple processors with multiples cores, or any combination thereof.

The memory/storage 1030 may include a memory 1032, such as a main memory, or other memory storage, and a storage unit 1036, both accessible to the processors 1010 such as via the bus 1002. The storage unit 1036 and memory 1032 store the instructions 1016 embodying any one or more of the methodologies or functions described herein. The instructions 1016 may also reside, completely or partially, within the memory 1032, within the storage unit 1036, within at least one of the processors 1010 (e.g., within the processor's cache memory), or any suitable combination thereof, during execution thereof by the machine 1000. Accordingly, the memory 1032, the storage unit 1036, and the memory of processors 1010 are examples of machine-readable media.

As used herein, "machine-readable medium" means a device able to store instructions and data temporarily or permanently and may include, but is not be limited to, random-access memory (RAM), read-only memory (ROM), buffer memory, flash memory, optical media, magnetic media, cache memory, other types of storage (e.g., Erasable Programmable Read-Only Memory (EEPROM)) and/or any suitable combination thereof. The term "machine-readable medium" should be taken to include a single medium or multiple media (e.g., a centralized or distributed database, or associated caches and servers) able to store instructions 1016. The term "machine-readable medium" shall also be taken to include any medium, or combination of multiple media, that is capable of storing instructions (e.g., instructions 1016) for execution by a machine (e.g., machine 1000), such that the instructions, when executed by one or more processors of the machine 1000 (e.g., processors 1010), cause the machine 1000 to perform any one or more of the methodologies described herein. Accordingly, a "machine-readable medium" refers to a single storage apparatus or device, as well as "cloud-based" storage systems or storage networks that include multiple storage apparatus or devices. The term "machine-readable medium" excludes signals per se.

The I/O components 1050 may include a wide variety of components to receive input, provide output, produce output, transmit information, exchange information, capture measurements, and so on. The specific I/O components 1050 that are included in a particular machine will depend on the type of machine. For example, portable machines such as mobile phones will likely include a touch input device or other such input mechanisms, while a headless server machine will likely not include such a touch input device. It will be appreciated that the I/O components 1050 may include many other components that are not shown in FIG. 9. The I/O components 1050 are grouped according to functionality merely for simplifying the following discussion and the grouping is in no way limiting. In various example embodiments, the I/O components 1050 may include output components 1052 and input components 1054. The output components 1052 may include visual components (e.g., a display such as a plasma display panel (PDP), a light emitting diode (LED) display, a liquid crystal display (LCD), a projector, or a cathode ray tube (CRT)), acoustic components (e.g., speakers), haptic components (e.g., a vibratory motor, resistance mechanisms), other signal generators, and so forth. The input components 1054 may include alphanumeric input components (e.g., a keyboard, a touch screen configured to receive alphanumeric input, a photo-optical keyboard, or other alphanumeric input components), point based input components (e.g., a mouse, a touchpad, a trackball, a joystick, a motion sensor, or other pointing instrument), tactile input components (e.g., a physical button, a touch screen that provides location and/or force of touches or touch gestures, or other tactile input components), audio input components (e.g., a microphone), and the like.

In further example embodiments, the I/O components 1050 may include biometric components 1056, motion components 1058, environmental components 1060, or position components 1062 among a wide array of other components. For example, the biometric components 1056 may include components to detect expressions (e.g., hand expressions, facial expressions, vocal expressions, body gestures, or eye tracking), measure biosignals (e.g., blood pressure, heart rate, body temperature, perspiration, or brain waves), identify a person (e.g., voice identification, retinal identification, facial identification, fingerprint identification, or electroencephalogram based identification), and the like. The motion components 1058 may include acceleration sensor components (e.g., accelerometer), gravitation sensor components, rotation sensor components (e.g., gyroscope), and so forth. The environmental components 1060 may include, for example, illumination sensor components (e.g., photometer), temperature sensor components (e.g., one or more thermometer that detect ambient temperature), humidity sensor components, pressure sensor components (e.g., barometer), acoustic sensor components (e.g., one or more microphones that detect background noise), proximity sensor components (e.g., infrared sensors that detect nearby objects), gas sensors (e.g., gas detection sensors to detection concentrations of hazardous gases for safety or to measure pollutants in the atmosphere), or other components that may provide indications, measurements, or signals corresponding to a surrounding physical environment. The position components 1062 may include location sensor components (e.g., a Global Position System (GPS) receiver component), altitude sensor components (e.g., altimeters or barometers that detect air pressure from which altitude may be derived), orientation sensor components (e.g., magnetometers), and the like.

Communication may be implemented using a wide variety of technologies. The I/O components 1050 may include communication components 1064 operable to couple the machine 1000 to a network 104 or devices 1070 via coupling 1082 and coupling 1072 respectively. For example, the communication components 1064 may include a network interface component or other suitable device to interface with the network 104. In further examples, communication components 1064 may include wired communication components, wireless communication components, cellular communication components, Near Field Communication (NFC) components, Bluetooth® components (e.g., Bluetooth® Low Energy), Wi-Fi® components, and other communication components to provide communication via other modalities. The devices 1070 may be another machine or any of a wide variety of peripheral devices (e.g., a peripheral device coupled via a Universal Serial Bus (USB)).

Moreover, the communication components 1064 may detect identifiers or include components operable to detect identifiers. For example, the communication components 1064 may include Radio Frequency Identification (RFID) tag reader components, NFC smart tag detection components, optical reader components (e.g., an optical sensor to detect one-dimensional bar codes such as Universal Product Code (UPC) bar code, multi-dimensional bar codes such as Quick Response (QR) code, Aztec code, Data Matrix, Dataglyph, MaxiCode, PDF417, Ultra Code, UCC RSS-2D bar code, and other optical codes), or acoustic detection components (e.g., microphones to identify tagged audio signals). In addition, a variety of information may be derived via the communication components 1064, such as, location via Internet Protocol (IP) geo-location, location via Wi-Fi® signal triangulation, location via detecting a NFC beacon signal that may indicate a particular location, and so forth.

Transmission Medium

In various example embodiments, one or more portions of the network 104 may be an ad hoc network, an intranet, an extranet, a virtual private network (VPN), a local area network (LAN), a wireless LAN (WLAN), a wide area network (WAN), a wireless WAN (WWAN), a metropolitan area network (MAN), the Internet, a portion of the Internet, a portion of the Public Switched Telephone Network (PSTN), a plain old telephone service (POTS) network, a cellular telephone network, a wireless network, a Wi-Fi® network, another type of network, or a combination of two or more such networks. For example, the network 104 or a portion of the network 104 may include a wireless or cellular network and the coupling 1082 may be a Code Division Multiple Access (CDMA) connection, a Global System for Mobile communications (GSM) connection, or other type of cellular or wireless coupling. In this example, the coupling 1082 may implement any of a variety of types of data transfer technology, such as Single Carrier Radio Transmission Technology (1xRTT), Evolution-Data Optimized (EVDO) technology, General Packet Radio Service (GPRS) technology, Enhanced Data rates for GSM Evolution (EDGE) technology, third Generation Partnership Project (3GPP) including 3G, fourth generation wireless (4G) networks, Universal Mobile Telecommunications System (UMTS), High Speed Packet Access (HSPA), Worldwide Interoperability for Microwave Access (WiMAX), Long Term Evolution (LTE) standard, others defined by various standard setting organizations, other long range protocols, or other data transfer technology.

The instructions 1016 may be transmitted or received over the network 104 using a transmission medium via a network interface device (e.g., a network interface component included in the communication components 1064) and utilizing any one of a number of well-known transfer protocols (e.g., hypertext transfer protocol (HTTP)). Similarly, the instructions 1016 may be transmitted or received using a transmission medium via the coupling 1072 (e.g., a peer-to-peer coupling) to devices 1070. The term "transmission medium" shall be taken to include any intangible medium that is capable of storing, encoding, or carrying instructions 1016 for execution by the machine 1000, and includes digital or analog communications signals or other intangible medium to facilitate communication of such software.

Language

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Although an overview of the inventive subject matter has been described with reference to specific example embodiments, various modifications and changes may be made to these embodiments without departing from the broader scope of embodiments of the present disclosure. Such embodiments of the inventive subject matter may be referred to herein, individually or collectively, by the term "invention" merely for convenience and without intending to voluntarily limit the scope of this application to any single disclosure or inventive concept if more than one is, in fact, disclosed.

The embodiments illustrated herein are described in sufficient detail to enable those skilled in the art to practice the teachings disclosed. Other embodiments may be used and derived therefrom, such that structural and logical substitutions and changes may be made without departing from the scope of this disclosure. The Detailed Description, therefore, is not to be taken in a limiting sense, and the scope of various embodiments is defined only by the appended claims, along with the full range of equivalents to which such claims are entitled.

As used herein, the term "or" may be construed in either an inclusive or exclusive sense. Moreover, plural instances may be provided for resources, operations, or structures described herein as a single instance. Additionally, boundaries between various resources, operations, modules, engines, and data stores are somewhat arbitrary, and particular operations are illustrated in a context of specific illustrative configurations. Other allocations of functionality are envisioned and may fall within a scope of various embodiments of the present disclosure. In general, structures and functionality presented as separate resources in the example configurations may be implemented as a combined structure or resource. Similarly, structures and functionality presented as a single resource may be implemented as separate resources. These and other variations, modifications, additions, and improvements fall within a scope of embodiments of the present disclosure as represented by the appended claims. The specification and drawings are, accordingly, to be regarded in an illustrative rather than a restrictive sense.

What is claimed is:

1. A mobile device, comprising:
   a housing having an integrated surface for swiping a magnetic swipe card;
   a magnetometer, positioned within the housing, for detecting direction and strength of magnetic fields to read magnetic information and to produce digital magnetometer output signals, the digital magnetometer output signals representing magnetic information derived from the magnetic swipe card and from the Earth's magnetic fields, each of the digital magnetometer output signals having a magnitude related to the strength of the detected magnetic fields;
   a memory device for storing instructions; and
   a processor coupled to the magnetometer, when executing the instructions, causes the mobile device to:
      determine at least some of the digital magnetometer output signals represent the magnetic information derived from the magnetic card information;
      determine at least some of the digital magnetometer output signals represent the magnetic information derived from the Earth's magnetic fields;
      provide the digital magnetometer output signals representing the magnetic information derived from the magnetic swipe card to a magnetic swipe card application for processing; and
      provide the digital magnetometer output signals representing the magnetic information derived from the Earth's magnetic information to a compass application for processing.

2. The mobile device of claim 1, wherein the magnetometer comprises a 3-axis electronic compass integrated circuit (IC).

3. The mobile device of claim 1, wherein the processor, when executing the instructions, further causes the mobile device to:
   filter the digital magnetometer output signals based on the magnitude of the digital magnetometer output signals.

4. The mobile device of claim 3,
   further comprising other magnetic components, included and within the housing; and
   wherein the processor, when executing the instructions, further causes the mobile device to:
      calculate magnetic deviation caused by the other magnetic components; and
      adjust the digital magnetometer output signals based on the calculated the magnetic deviation components prior to executing the instructions that causes the mobile device to filter the digital magnetometer output signals based on the magnitude of the digital magnetometer output signals.

5. The mobile device of claim 1, wherein the processor, when executing the instructions to determine at least some of the digital magnetometer signals represent the magnetic information derived from the magnetic swipe card, further causes the mobile device to:
   filter the digital magnetometer output signals based on the magnitude of the digital magnetometer output signals related to a range of the detected magnetic field strengths read from the magnetic information.

6. The mobile device of claim 1, wherein the processor, when executing the instructions to determine at least some of the digital magnetometer output signals represent the magnetic information derived from the Earth's magnetic fields, further causes the mobile device to:
   filter the digital magnetometer output signals based on the magnitude of the digital magnetometer output signals related to a range of the magnetic fields strengths associated with the Earth, the range represents at least 20,000 to 80,000 nanoteslas (nTs).

7. The mobile device of claim 1, wherein the digital magnetometer output signals includes selectable data output signals for each of three axis magnetic components.

8. The mobiles device of claim 1, wherein the compass application represents a navigation application.

9. The mobile device of claim 1,
   wherein the digital magnetometer output signals represents magnetic information derived from medical information; and
   wherein the processor, when executing the instructions further causes the mobile device to:
      determine at least some of the digital magnetometer output signals represent magnetic information derived from the medical information; and
      provide the digital magnetometer output signals representing magnetic information derived from the medical information to another application for processing.

10. A method, comprising:
    detecting, by a magnetometer within a mobile device, direction and strength of magnetic fields from a magnetic swipe card that were swiped along a surface of the mobile device;
    detecting, by the magnetometer within the mobile device, direction and strength of magnetic fields from an other magnetic source;
    generating, by the magnetometer within the mobile device, digital magnetometer output signals, the digital magnetometer output signals representing magnetic information derived from the magnetic swipe card and from the other magnetic source, each of the digital magnetometer output signals having a magnitude related to the strength of the detected magnetic fields;
    determining, by a processor of a machine, at least some of the digital magnetometer output signals represent the detected magnetic information derived from the magnetic swipe card;
    determining, by a processor of a machine, at least some of the digital magnetometer output signals represent the detected magnetic information from the other magnetic source; and
    executing, by a processor of a machine, at least one of a magnetic card application utilizing the digital magnetometer output signals representing the detected magnetic information derived from the magnetic swipe card and an other application utilizing the digital magnetometer output signals representing the detected magnetic information derived the other magnetic source.

11. The method of claim 10, further comprising:
    storing the digital magnetometer output signals;
    accessing, by the processor of the machine, the digital magnetometer output signals representing the detected magnetic information derived from the magnetic swipe card based on instructions from the magnetic card application; and
    accessing, by the processor of the machine, the digital magnetometer output signals representing the detected magnetic information derived the other magnetic source based on the other application.

12. The method of claim 10, wherein at least some of the digital magnetometer output signals represent the detected magnetic information derived from the magnetic swipe card further comprises:

filtering the digital magnetometer output signals based on the magnitude of the digital magnetometer output signals.

13. The method of claim 10, wherein determining least some of the digital magnetometer output signals represent the magnetic information derived from the magnetic card information further comprises:

filtering the digital magnetometer output signals based on the magnitude of the digital magnetometer output signals related to a range of the detected magnetic field strengths read from the magnetic information.

14. The method of claim 10, wherein determining at least some of the digital magnetometer output signals represent the detected magnetic information from the other magnetic source further comprises:

filtering the digital magnetometer output signals based on the magnitude of the digital magnetometer output signals related to a range of the magnetic fields strengths associated with the Earth, the range represents at least 20,000 to 80,000 nanoteslas (nTs).

15. The method of claim 10, further comprising:

determining at least some of the digital magnetometer output signals represent magnetic information derived from medical information; and providing the digital magnetometer output signals representing magnetic information derived from the medical information to a medical application for processing.

16. The method of claim 15, wherein determining at least some of the digital magnetometer output signals represent magnetic information derived from medical information further comprises:

determining at least some of the digital magnetometer output signals represent magnetic information derived from blood samples.

17. A non-transitory machine-readable storage medium in communication with at least one processor, the machine-readable storage medium storing instructions which, when executed by the at least one processor, performs operations comprising:

receiving digital magnetometer output signals captured by a mobile device, the digital magnetometer output signals including magnetic information derived from a magnetic swipe card and Earth's magnetic field;

filtering the magnetic information to determine whether the digital magnetometer output signals represents magnetic information associated with the magnetic swipe card or magnetic information associated with the Earth's magnetic fields based on a magnitude of the digital magnetometer output signals;

providing the digital magnetometer output signals representing the magnetic information associated with the magnetic swipe card to a magnetic swipe card application for processing; and providing the digital magnetometer output signals representing the magnetic information associated with the Earth's magnetic fields to a compass application for processing.

18. The non-transitory machine-readable storage medium of claim 17 which, when executed by the at least one processor, performs operations further comprising:

receiving digital magnetometer output signals captured by a mobile device, the digital magnetometer output signals including magnetic information derived from medical information;

determining at least some of the digital magnetometer output signals represent magnetic information associated with the medical information; and providing the digital magnetometer output signals representing magnetic information associated with medical information to the medical application for processing.

* * * * *